(12) United States Patent
Williams

(10) Patent No.: US 11,759,207 B2
(45) Date of Patent: Sep. 19, 2023

(54) SURGICAL STAPLING APPARATUS WITH ADJUSTABLE HEIGHT CLAMPING MEMBER

(71) Applicant: Covidien LP, Mansfield, MA (US)

(72) Inventor: Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 324 days.

(21) Appl. No.: 17/159,357

(22) Filed: Jan. 27, 2021

(65) Prior Publication Data

US 2022/0233192 A1 Jul. 28, 2022

(51) Int. Cl.
*A61B 17/072* (2006.01)

(52) U.S. Cl.
CPC .... *A61B 17/072* (2013.01); *A61B 2017/0725* (2013.01); *A61B 2017/07257* (2013.01); *A61B 2017/07271* (2013.01); *A61B 2017/07278* (2013.01); *A61B 2017/07285* (2013.01)

(58) Field of Classification Search
CPC .......... A61B 17/072; A61B 2017/0725; A61B 2017/07257; A61B 2017/07271; A61B 2017/07278
USPC ...................................................... 227/176.1
See application file for complete search history.

(56) References Cited

U.S. PATENT DOCUMENTS

| | | | |
|---|---|---|---|
| 3,499,591 A | 3/1970 | Green | |
| 3,777,538 A | 12/1973 | Weatherly et al. | |
| 3,882,854 A | 5/1975 | Hulka et al. | |
| 4,027,510 A | 6/1977 | Hiltebrandt | |
| 4,086,926 A | 5/1978 | Green et al. | |
| 4,241,861 A | 12/1980 | Fleischer | |
| 4,244,372 A | 1/1981 | Kapitanov et al. | |
| 4,429,695 A | 2/1984 | Green | |
| 4,505,414 A | 3/1985 | Filipi | |
| 4,520,817 A | 6/1985 | Green | |

(Continued)

FOREIGN PATENT DOCUMENTS

| AU | 198654765 | 9/1986 |
|---|---|---|
| CA | 2773414 A1 | 11/2012 |

(Continued)

OTHER PUBLICATIONS

Extended European Search Report for application No. 22153619.6 dated Jul. 1, 2022.

(Continued)

*Primary Examiner* — Valentin Neacsu
(74) *Attorney, Agent, or Firm* — Carter, DeLuca & Farrell LLP

(57) ABSTRACT

A surgical stapling device includes a jaw assembly including a first jaw supporting an anvil assembly and a second jaw supporting a cartridge assembly. A drive assembly is translatable through the jaw assembly to effect the clamping and stapling of tissue. The drive assembly includes a clamping member and an adjustment member. The clamping member includes a first clamping surface configured to engage the anvil assembly. The adjustment member includes a second clamping surface configured to engage the staple cartridge. The first clamping surface is spaced from the second clamping surface to define a clamping height. The adjustment member is moveable relative to the clamping member between a first position and a second position to change the clamping height.

17 Claims, 21 Drawing Sheets

(56) References Cited

U.S. PATENT DOCUMENTS

| | | |
|---|---|---|
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Ley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |

(56) References Cited

U.S. PATENT DOCUMENTS

| | | |
|---|---|---|
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Ley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Billner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,690,675 A | 11/1997 | Sawyer et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Billner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,817,509 B2 | 11/2004 | Geiste et al. |
| 6,830,174 B2 | 12/2004 | Hillstead et al. |

(56) References Cited

U.S. PATENT DOCUMENTS

| | | |
|---|---|---|
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,267,682 B1 | 9/2007 | Bender et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |

(56) References Cited

U.S. PATENT DOCUMENTS

| | | |
|---|---|---|
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,896 B2 | 10/2010 | Racenet |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,630 B2 | 11/2010 | Damadian et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |

(56) References Cited

U.S. PATENT DOCUMENTS

| | | | |
|---|---|---|---|
| 7,963,433 | B2 | 6/2011 | Whitman et al. |
| 7,967,178 | B2 | 6/2011 | Scirica et al. |
| 7,967,179 | B2 | 6/2011 | Olson et al. |
| 7,967,180 | B2 | 6/2011 | Scirica |
| 7,975,894 | B2 | 7/2011 | Boyden et al. |
| 7,980,443 | B2 | 7/2011 | Scheib et al. |
| 7,988,026 | B2 | 8/2011 | Knodel et al. |
| 7,988,027 | B2 | 8/2011 | Olson et al. |
| 7,988,028 | B2 | 8/2011 | Farascioni et al. |
| 7,992,758 | B2 | 8/2011 | Whitman et al. |
| 7,997,468 | B2 | 8/2011 | Farascioni |
| 7,997,469 | B2 | 8/2011 | Olson et al. |
| 8,002,795 | B2 | 8/2011 | Beetel |
| 8,006,885 | B2 | 8/2011 | Marczyk |
| 8,006,887 | B2 | 8/2011 | Marczyk |
| 8,007,505 | B2 | 8/2011 | Weller et al. |
| 8,007,513 | B2 | 8/2011 | Nalagatla et al. |
| 8,011,550 | B2 | 9/2011 | Aranyi et al. |
| 8,011,551 | B2 | 9/2011 | Marczyk et al. |
| 8,011,552 | B2 | 9/2011 | Ivanko |
| 8,011,553 | B2 | 9/2011 | Mastri et al. |
| 8,011,555 | B2 | 9/2011 | Tarinelli et al. |
| 8,012,170 | B2 | 9/2011 | Whitman et al. |
| 8,015,976 | B2 | 9/2011 | Shah |
| 8,016,177 | B2 | 9/2011 | Bettuchi et al. |
| 8,016,178 | B2 | 9/2011 | Olson et al. |
| 8,020,742 | B2 | 9/2011 | Marczyk |
| 8,020,743 | B2 | 9/2011 | Shelton, IV |
| 8,028,882 | B2 | 10/2011 | Viola |
| 8,028,883 | B2 | 10/2011 | Stopek |
| 8,028,884 | B2 | 10/2011 | Sniffin et al. |
| 8,033,438 | B2 | 10/2011 | Scirica |
| 8,033,440 | B2 | 10/2011 | Wenchell et al. |
| 8,033,441 | B2 | 10/2011 | Marczyk |
| 8,033,442 | B2 | 10/2011 | Racenet et al. |
| 8,034,077 | B2 | 10/2011 | Smith et al. |
| 8,038,044 | B2 | 10/2011 | Viola |
| 8,038,045 | B2 | 10/2011 | Bettuchi et al. |
| 8,052,024 | B2 | 11/2011 | Viola et al. |
| 8,056,787 | B2 | 11/2011 | Boudreaux et al. |
| 8,056,788 | B2 | 11/2011 | Mastri et al. |
| 8,056,791 | B2 | 11/2011 | Whitman |
| 8,061,577 | B2 | 11/2011 | Racenet et al. |
| 8,066,166 | B2 | 11/2011 | Demmy et al. |
| 8,070,033 | B2 | 12/2011 | Milliman et al. |
| 8,070,034 | B1 | 12/2011 | Knodel |
| 8,070,035 | B2 | 12/2011 | Holsten et al. |
| 8,074,858 | B2 | 12/2011 | Marczyk |
| 8,074,859 | B2 | 12/2011 | Kostrzewski |
| 8,074,862 | B2 | 12/2011 | Shah |
| 8,083,118 | B2 | 12/2011 | Milliman et al. |
| 8,083,119 | B2 | 12/2011 | Prommersberger |
| 8,083,120 | B2 | 12/2011 | Shelton, IV et al. |
| 8,087,563 | B2 | 1/2012 | Milliman et al. |
| 8,091,753 | B2 | 1/2012 | Viola |
| 8,091,754 | B2 | 1/2012 | Ehrenfels et al. |
| 8,091,756 | B2 | 1/2012 | Viola |
| 8,092,493 | B2 | 1/2012 | Marczyk |
| 8,096,459 | B2 | 1/2012 | Ortiz et al. |
| 8,096,460 | B2 | 1/2012 | Blier et al. |
| 8,100,309 | B2 | 1/2012 | Marczyk |
| 8,100,310 | B2 | 1/2012 | Zemlok |
| 8,102,008 | B2 | 1/2012 | Wells |
| 8,113,406 | B2 | 2/2012 | Holsten et al. |
| 8,113,407 | B2 | 2/2012 | Holsten et al. |
| 8,113,408 | B2 | 2/2012 | Wenchell et al. |
| 8,113,409 | B2 | 2/2012 | Cohen et al. |
| 8,113,410 | B2 | 2/2012 | Hall et al. |
| 8,123,101 | B2 | 2/2012 | Racenet et al. |
| 8,127,975 | B2 | 3/2012 | Olson et al. |
| 8,127,976 | B2 | 3/2012 | Scirica et al. |
| 8,132,703 | B2 | 3/2012 | Milliman et al. |
| 8,132,705 | B2 | 3/2012 | Viola et al. |
| 8,132,706 | B2 | 3/2012 | Marczyk et al. |
| 8,136,713 | B2 | 3/2012 | Hathaway et al. |
| 8,141,762 | B2 | 3/2012 | Bedi et al. |
| 8,152,041 | B2 | 4/2012 | Kostrzewski |
| 8,157,148 | B2 | 4/2012 | Scirica |
| 8,157,150 | B2 | 4/2012 | Viola et al. |
| 8,157,151 | B2 | 4/2012 | Ingmanson et al. |
| 8,157,152 | B2 | 4/2012 | Holsten et al. |
| 8,162,197 | B2 | 4/2012 | Mastri et al. |
| 8,167,185 | B2 | 5/2012 | Shelton, IV et al. |
| 8,167,186 | B2 | 5/2012 | Racenet et al. |
| 8,172,121 | B2 | 5/2012 | Krehel |
| 8,172,124 | B2 | 5/2012 | Shelton, IV et al. |
| 8,181,837 | B2 | 5/2012 | Roy |
| 8,186,555 | B2 | 5/2012 | Shelton, IV et al. |
| 8,186,557 | B2 | 5/2012 | Cohen et al. |
| 8,186,558 | B2 | 5/2012 | Sapienza |
| 8,186,559 | B1 | 5/2012 | Whitman |
| 8,186,560 | B2 | 5/2012 | Hess et al. |
| 8,193,044 | B2 | 6/2012 | Kenneth |
| 8,196,795 | B2 | 6/2012 | Moore et al. |
| 8,196,796 | B2 | 6/2012 | Shelton, IV et al. |
| 8,201,721 | B2 | 6/2012 | Zemlok et al. |
| 8,205,619 | B2 | 6/2012 | Shah et al. |
| 8,205,780 | B2 | 6/2012 | Sorrentino et al. |
| 8,205,781 | B2 | 6/2012 | Baxter, III et al. |
| 8,210,412 | B2 | 7/2012 | Marczyk |
| 8,210,416 | B2 | 7/2012 | Milliman et al. |
| 8,215,532 | B2 | 7/2012 | Marczyk |
| 8,216,236 | B2 | 7/2012 | Heinrich et al. |
| 8,220,688 | B2 | 7/2012 | Laurent et al. |
| 8,220,690 | B2 | 7/2012 | Hess et al. |
| 8,225,979 | B2 | 7/2012 | Farascioni et al. |
| 8,231,040 | B2 | 7/2012 | Zemlok et al. |
| 8,231,041 | B2 | 7/2012 | Marczyk et al. |
| 8,235,272 | B2 | 8/2012 | Nicholas et al. |
| 8,235,273 | B2 | 8/2012 | Olson et al. |
| 8,235,274 | B2 | 8/2012 | Cappola |
| 8,236,010 | B2 | 8/2012 | Ortiz et al. |
| 8,240,536 | B2 | 8/2012 | Marczyk |
| 8,240,537 | B2 | 8/2012 | Marczyk |
| 8,241,322 | B2 | 8/2012 | Whitman et al. |
| 8,245,897 | B2 | 8/2012 | Tzakis et al. |
| 8,245,898 | B2 | 8/2012 | Smith et al. |
| 8,245,899 | B2 | 8/2012 | Swensgard et al. |
| 8,245,931 | B2 | 8/2012 | Shigeta |
| 8,252,009 | B2 | 8/2012 | Weller et al. |
| 8,256,653 | B2 | 9/2012 | Farascioni |
| 8,256,654 | B2 | 9/2012 | Bettuchi et al. |
| 8,256,655 | B2 | 9/2012 | Sniffin et al. |
| 8,256,656 | B2 | 9/2012 | Milliman et al. |
| 8,267,300 | B2 | 9/2012 | Boudreaux |
| 8,272,551 | B2 | 9/2012 | Knodel et al. |
| 8,272,553 | B2 | 9/2012 | Mastri et al. |
| 8,272,554 | B2 | 9/2012 | Whitman et al. |
| 8,276,594 | B2 | 10/2012 | Shah |
| 8,276,801 | B2 | 10/2012 | Zemlok et al. |
| 8,281,973 | B2 | 10/2012 | Wenchell et al. |
| 8,286,847 | B2 | 10/2012 | Taylor |
| 8,286,848 | B2 | 10/2012 | Wenchell et al. |
| 8,286,850 | B2 | 10/2012 | Viola |
| 8,292,146 | B2 | 10/2012 | Holsten et al. |
| 8,292,147 | B2 | 10/2012 | Viola |
| 8,292,148 | B2 | 10/2012 | Viola |
| 8,292,149 | B2 | 10/2012 | Ivanko |
| 8,292,150 | B2 | 10/2012 | Bryant |
| 8,292,151 | B2 | 10/2012 | Viola |
| 8,292,152 | B2 | 10/2012 | Milliman et al. |
| 8,292,153 | B2 | 10/2012 | Jankowski |
| 8,292,154 | B2 | 10/2012 | Marczyk |
| 8,292,155 | B2 | 10/2012 | Shelton, IV et al. |
| 8,292,156 | B2 | 10/2012 | Kostrzewski |
| 8,292,158 | B2 | 10/2012 | Sapienza |
| 8,308,040 | B2 | 11/2012 | Huang et al. |
| 8,308,041 | B2 | 11/2012 | Kostrzewski |
| 8,308,042 | B2 | 11/2012 | Aranyi |
| 8,308,043 | B2 | 11/2012 | Bindra et al. |
| 8,308,044 | B2 | 11/2012 | Viola |
| 8,308,046 | B2 | 11/2012 | Prommersberger |
| 8,308,757 | B2 | 11/2012 | Hillstead et al. |
| 8,317,070 | B2 | 11/2012 | Hueil et al. |

(56) References Cited

U.S. PATENT DOCUMENTS

| | | |
|---|---|---|
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czemik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,240 B1 | 8/2013 | Mata et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 | 11/2013 | Shelton, IV et al. |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,515 B2 | 12/2013 | Okoniewski |
| 8,597,311 B2 | 12/2013 | Criscuolo et al. |
| 8,602,288 B2 | 12/2013 | Shelton, IV et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | (Prommersberger) Stopek et al. |
| 8,627,994 B2 | 1/2014 | Zemlok et al. |
| 8,628,544 B2 | 1/2014 | Farascioni |
| 8,631,988 B2 | 1/2014 | Viola |

(56) References Cited

U.S. PATENT DOCUMENTS

| | | |
|---|---|---|
| 8,631,989 B2 | 1/2014 | Aranyi et al. |
| 8,631,991 B2 | 1/2014 | Cropper et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,684,253 B2 | 4/2014 | Giordano et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,701,961 B2 | 4/2014 | Ivanko |
| 8,708,213 B2 | 4/2014 | Shelton, IV et al. |
| 8,714,429 B2 | 5/2014 | Demmy |
| 8,715,277 B2 | 5/2014 | Weizman |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,752,748 B2 | 6/2014 | Whitman et al. |
| 8,752,749 B2 | 6/2014 | Moore et al. |
| 8,757,465 B2 | 6/2014 | Woodard, Jr. et al. |
| 8,758,391 B2 | 6/2014 | Swayze et al. |
| 8,763,875 B2 | 7/2014 | Morgan et al. |
| 8,763,876 B2 | 7/2014 | Kostrzewski |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,833,631 B2 | 9/2014 | Munro, III et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,788 B2 | 9/2014 | Knodel |
| 8,851,354 B2 | 10/2014 | Swensgard et al. |
| 8,851,355 B2 | 10/2014 | Aranyi et al. |
| 8,857,693 B2 | 10/2014 | Schuckmann et al. |
| 8,864,007 B2 | 10/2014 | Widenhouse et al. |
| 8,864,009 B2 | 10/2014 | Shelton, IV et al. |
| 8,864,010 B2 | 10/2014 | Williams |
| 8,870,050 B2 | 10/2014 | Hodgkinson |
| 8,875,971 B2 | 11/2014 | Hall et al. |
| 8,875,972 B2 | 11/2014 | Weisenburgh, II et al. |
| 8,893,949 B2 | 11/2014 | Shelton, IV et al. |
| 8,893,950 B2 | 11/2014 | Marczyk |
| 8,899,461 B2 | 12/2014 | Farascioni |
| 8,899,462 B2 | 12/2014 | Kostrzewski et al. |
| 8,899,463 B2 | 12/2014 | Schall et al. |
| 8,899,464 B2 | 12/2014 | Hueil et al. |
| 8,900,616 B2 | 12/2014 | Belcheva et al. |
| 8,920,435 B2 | 12/2014 | Smith et al. |
| 8,925,782 B2 | 1/2015 | Shelton, IV |
| 8,926,598 B2 | 1/2015 | Mollere et al. |
| 8,931,681 B2 | 1/2015 | Kostrzewski |
| 8,931,682 B2 | 1/2015 | Timm et al. |
| 8,931,693 B1 | 1/2015 | Kumar et al. |
| 8,955,732 B2 | 2/2015 | Zemlok et al. |
| 8,958,429 B2 | 2/2015 | Shukla et al. |
| 8,960,517 B2 | 2/2015 | Lee |
| 8,967,443 B2 | 3/2015 | McCuen |
| 8,967,446 B2 | 3/2015 | Beardsley et al. |
| 8,973,803 B2 | 3/2015 | Hall et al. |
| 8,978,954 B2 | 3/2015 | Shelton, IV et al. |
| 8,978,956 B2 | 3/2015 | Schall et al. |
| 8,991,677 B2 | 3/2015 | Moore et al. |
| 8,991,678 B2 | 3/2015 | Wellman et al. |
| 8,998,058 B2 | 4/2015 | Moore et al. |
| 8,998,060 B2 | 4/2015 | Bruewer et al. |
| 9,005,230 B2 | 4/2015 | Yates et al. |
| 9,010,606 B2 | 4/2015 | Aranyi et al. |
| 9,010,607 B2 | 4/2015 | Kostrzewski |
| 9,010,610 B2 | 4/2015 | Hodgkinson |
| 9,016,539 B2 | 4/2015 | Kostrzewski et al. |
| 9,016,541 B2 | 4/2015 | Viola et al. |
| 9,016,542 B2 | 4/2015 | Shelton, IV et al. |
| 9,016,544 B2 | 4/2015 | Hodgkinson et al. |
| 9,016,545 B2 | 4/2015 | Aranyi et al. |
| 9,016,546 B2 | 4/2015 | Demmy et al. |
| 9,022,271 B2 | 5/2015 | Scirica |
| 9,027,817 B2 | 5/2015 | Milliman et al. |
| 9,033,203 B2 | 5/2015 | Woodard, Jr. et al. |
| 9,044,228 B2 | 6/2015 | Woodard, Jr. et al. |
| 9,044,229 B2 | 6/2015 | Scheib et al. |
| 9,050,084 B2 | 6/2015 | Schmid et al. |
| 9,055,941 B2 | 6/2015 | Schmid et al. |
| 9,060,770 B2 | 6/2015 | Shelton, IV et al. |
| 9,072,535 B2 | 7/2015 | Shelton, IV et al. |
| 9,084,601 B2 | 7/2015 | Moore et al. |
| 9,089,326 B2 | 7/2015 | Krumanaker et al. |
| 9,095,339 B2 | 8/2015 | Moore et al. |
| 9,101,359 B2 | 8/2015 | Smith et al. |
| 9,107,663 B2 | 8/2015 | Swensgard |
| 9,107,664 B2 | 8/2015 | Marczyk |
| 9,107,667 B2 | 8/2015 | Hodgkinson |
| 9,113,862 B2 | 8/2015 | Morgan et al. |
| 9,113,864 B2 | 8/2015 | Morgan et al. |
| 9,113,870 B2 | 8/2015 | Viola |
| 9,113,872 B2 | 8/2015 | Viola |
| 9,113,880 B2 | 8/2015 | Zemlok et al. |
| 9,125,649 B2 | 9/2015 | Bruewer et al. |
| 9,138,225 B2 | 9/2015 | Huang et al. |
| 9,155,537 B2 | 10/2015 | Katre et al. |
| 9,179,912 B2 | 11/2015 | Yates et al. |
| 9,192,378 B2 | 11/2015 | Aranyi et al. |
| 9,192,379 B2 | 11/2015 | Aranyi et al. |
| 9,192,384 B2 | 11/2015 | Bettuchi |
| 9,198,644 B2 | 12/2015 | Balek et al. |
| 9,198,660 B2 | 12/2015 | Hodgkinson |
| 9,198,661 B2 | 12/2015 | Swensgard |
| 9,198,662 B2 | 12/2015 | Barton et al. |
| 9,204,876 B2 | 12/2015 | Cappola et al. |
| 9,204,880 B2 | 12/2015 | Baxter, III et al. |
| 9,216,019 B2 | 12/2015 | Schmid et al. |

(56) References Cited

U.S. PATENT DOCUMENTS

| | | | |
|---|---|---|---|
| 9,216,020 B2 | 12/2015 | Zhang et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,232,941 B2 | 1/2016 | Mandakolathur Vasudevan et al. |
| 9,232,944 B2 | 1/2016 | Cappola et al. |
| 9,237,891 B2 | 1/2016 | Shelton, IV |
| 9,237,892 B2 | 1/2016 | Hodgkinson |
| 9,254,180 B2 | 2/2016 | Huitema et al. |
| 9,265,585 B2 | 2/2016 | Wingardner et al. |
| 9,271,728 B2 | 3/2016 | Gupta et al. |
| 9,272,406 B2 | 3/2016 | Aronhalt et al. |
| 9,277,919 B2 | 3/2016 | Timmer et al. |
| 9,282,962 B2 | 3/2016 | Schmid et al. |
| 9,283,054 B2 | 3/2016 | Morgan et al. |
| 9,289,209 B2 | 3/2016 | Gurumurthy et al. |
| 9,289,210 B2 | 3/2016 | Baxter, III et al. |
| 9,289,225 B2 | 3/2016 | Shelton, IV et al. |
| 9,295,464 B2 | 3/2016 | Shelton, IV et al. |
| 9,295,465 B2 | 3/2016 | Farascioni |
| 9,301,752 B2 | 4/2016 | Mandakolathur Vasudevan et al. |
| 9,301,753 B2 | 4/2016 | Aldridge et al. |
| 9,301,757 B2 | 4/2016 | Williams |
| 9,307,965 B2 | 4/2016 | Ming et al. |
| 9,307,986 B2 | 4/2016 | Hall et al. |
| 9,307,989 B2 | 4/2016 | Shelton, IV et al. |
| 9,314,246 B2 | 4/2016 | Shelton, IV et al. |
| 9,320,518 B2 | 4/2016 | Henderson et al. |
| 9,320,521 B2 | 4/2016 | Shelton, IV et al. |
| 9,320,523 B2 | 4/2016 | Shelton, IV et al. |
| 9,326,767 B2 | 5/2016 | Koch, Jr. et al. |
| 9,332,987 B2 | 5/2016 | Leimbach et al. |
| 9,345,477 B2 | 5/2016 | Anim et al. |
| 9,345,478 B2 | 5/2016 | Knodel |
| 9,345,481 B2 | 5/2016 | Hall et al. |
| 9,345,780 B2 | 5/2016 | Manoharan et al. |
| 9,351,727 B2 | 5/2016 | Leimbach et al. |
| 9,351,732 B2 | 5/2016 | Hodgkinson |
| 9,358,003 B2 | 6/2016 | Hall et al. |
| 9,364,217 B2 | 6/2016 | Kostrzewski et al. |
| 9,364,218 B2 | 6/2016 | Scirica |
| 9,364,219 B2 | 6/2016 | Olson et al. |
| 9,364,220 B2 | 6/2016 | Williams |
| 9,364,227 B2 | 6/2016 | Kostrzewski |
| 9,364,231 B2 | 6/2016 | Wenchell |
| 9,364,233 B2 | 6/2016 | Alexander, III et al. |
| 9,370,358 B2 | 6/2016 | Shelton, IV et al. |
| 9,370,362 B2 | 6/2016 | Petty et al. |
| 9,386,983 B2 | 7/2016 | Swensgard et al. |
| 9,386,984 B2 | 7/2016 | Aronhalt et al. |
| 9,386,988 B2 | 7/2016 | Baxter, III et al. |
| 9,393,018 B2 | 7/2016 | Wang et al. |
| 9,398,911 B2 | 7/2016 | Auld |
| 9,402,604 B2 | 8/2016 | Williams et al. |
| 9,421,014 B2 | 8/2016 | Ingmanson et al. |
| 9,433,419 B2 | 9/2016 | Gonzalez et al. |
| 9,433,420 B2 | 9/2016 | Hodgkinson |
| 9,445,810 B2 | 9/2016 | Cappola |
| 9,445,813 B2 | 9/2016 | Shelton, IV et al. |
| 9,451,959 B2 | 9/2016 | Patankar et al. |
| 9,468,438 B2 | 10/2016 | Baber et al. |
| 9,468,439 B2 | 10/2016 | Cappola et al. |
| 9,480,476 B2 | 11/2016 | Aldridge et al. |
| 9,480,492 B2 | 11/2016 | Aranyi et al. |
| 9,492,171 B2 | 11/2016 | Patenaude |
| 9,498,212 B2 | 11/2016 | Racenet et al. |
| 9,498,219 B2 | 11/2016 | Moore et al. |
| 9,510,827 B2 | 12/2016 | Kostrzewski |
| 9,517,065 B2 | 12/2016 | Simms et al. |
| 9,517,066 B2 | 12/2016 | Racenet et al. |
| 9,539,007 B2 | 1/2017 | Dhakad et al. |
| 9,549,735 B2 | 1/2017 | Shelton, IV et al. |
| 9,561,031 B2 | 2/2017 | Heinrich et al. |
| 9,597,077 B2 | 3/2017 | Hodgkinson |
| 9,610,080 B2 | 4/2017 | Whitfield et al. |
| 9,913,646 B2 | 3/2018 | Shelton, IV |
| 9,936,954 B2 | 4/2018 | Shelton, IV et al. |
| 9,987,099 B2 | 6/2018 | Chen et al. |
| 10,004,497 B2 | 6/2018 | Overmyer et al. |
| 10,004,505 B2 | 6/2018 | Moore et al. |
| 10,045,782 B2 | 8/2018 | Murthy Aravalli |
| 10,064,622 B2 | 9/2018 | Murthy Aravalli |
| 10,076,325 B2 | 9/2018 | Huang et al. |
| 10,135,242 B2 | 11/2018 | Baber et al. |
| 10,143,474 B2 | 12/2018 | Bucciaglia et al. |
| 10,172,615 B2 | 1/2019 | Marczyk et al. |
| 10,206,677 B2 | 2/2019 | Harris et al. |
| 10,265,066 B2 | 4/2019 | Measamer et al. |
| 10,265,074 B2 | 4/2019 | Shelton, IV et al. |
| 10,271,841 B2 | 4/2019 | Overmyer et al. |
| 10,327,776 B2 | 6/2019 | Harris et al. |
| 10,349,941 B2 | 7/2019 | Marczyk et al. |
| 10,390,828 B2 | 8/2019 | Vendely et al. |
| 10,405,857 B2 | 9/2019 | Shelton |
| 10,463,368 B2 | 11/2019 | Kostrzewski |
| 10,478,182 B2 | 11/2019 | Taylor |
| 10,478,183 B2 | 11/2019 | Hess et al. |
| 10,548,599 B2 | 2/2020 | Marczyk et al. |
| 11,534,166 B2 * | 12/2022 | Bucciaglia ....... A61B 17/07207 |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0006429 A1 | 1/2005 | Wales et al. |
| 2005/0216055 A1 | 9/2005 | Scirica et al. |
| 2006/0049229 A1 | 3/2006 | Milliman et al. |
| 2006/0180634 A1 | 8/2006 | Shelton et al. |
| 2006/0289602 A1 | 12/2006 | Wales et al. |
| 2007/0073340 A1 * | 3/2007 | Shelton, IV ..... A61B 17/07207 227/175.1 |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0082124 A1 * | 4/2008 | Hess .................... A61B 17/115 606/219 |
| 2008/0110961 A1 | 5/2008 | Voegele et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0090763 A1 | 4/2009 | Zemlok et al. |
| 2009/0090766 A1 | 4/2009 | Knodel |
| 2009/0242610 A1 | 10/2009 | Shelton, IV et al. |
| 2009/0255974 A1 | 10/2009 | Viola |
| 2009/0308907 A1 | 12/2009 | Nalagatla et al. |
| 2010/0012703 A1 | 1/2010 | Calabrese et al. |
| 2010/0051669 A1 | 3/2010 | Milliman |
| 2010/0069942 A1 | 3/2010 | Shelton, IV |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |

(56) References Cited

U.S. PATENT DOCUMENTS

| | | |
|---|---|---|
| 2010/0193566 A1 | 8/2010 | Scheib et al. |
| 2010/0224668 A1 | 9/2010 | Fontayne et al. |
| 2010/0249802 A1 | 9/2010 | May et al. |
| 2010/0252611 A1 | 10/2010 | Ezzat et al. |
| 2011/0006101 A1 | 1/2011 | Hall et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0087276 A1 | 4/2011 | Bedi et al. |
| 2011/0101069 A1 | 5/2011 | Bombard et al. |
| 2011/0114702 A1 | 5/2011 | Farascioni |
| 2011/0121049 A1 | 5/2011 | Malinouskas et al. |
| 2011/0147433 A1 | 6/2011 | Shelton, IV et al. |
| 2011/0155787 A1 | 6/2011 | Baxter, III et al. |
| 2011/0163146 A1 | 7/2011 | Ortiz et al. |
| 2011/0163149 A1 | 7/2011 | Viola |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0204119 A1 | 8/2011 | McCuen |
| 2011/0278343 A1 | 11/2011 | Knodel et al. |
| 2011/0290856 A1 | 12/2011 | Shelton, IV et al. |
| 2012/0053406 A1 | 3/2012 | Conlon et al. |
| 2012/0061446 A1 | 3/2012 | Knodel et al. |
| 2012/0074200 A1 | 3/2012 | Schmid et al. |
| 2012/0080478 A1 | 4/2012 | Morgan et al. |
| 2012/0080495 A1 | 4/2012 | Holcomb et al. |
| 2012/0080498 A1 | 4/2012 | Shelton, IV et al. |
| 2012/0091183 A1 | 4/2012 | Manoux et al. |
| 2012/0138659 A1 | 6/2012 | Marczyk et al. |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199632 A1 | 8/2012 | Spivey et al. |
| 2012/0211542 A1 | 8/2012 | Racenet |
| 2012/0223121 A1 | 9/2012 | Viola et al. |
| 2012/0234895 A1 | 9/2012 | O'Connor et al. |
| 2012/0234897 A1 | 9/2012 | Shelton, IV et al. |
| 2012/0241492 A1 | 9/2012 | Shelton, IV et al. |
| 2012/0241493 A1 | 9/2012 | Baxter, III et al. |
| 2012/0241504 A1 | 9/2012 | Soltz et al. |
| 2012/0248169 A1 | 10/2012 | Widenhouse et al. |
| 2012/0286021 A1 | 11/2012 | Kostrzewski |
| 2012/0286022 A1 | 11/2012 | Olson et al. |
| 2012/0298722 A1 | 11/2012 | Hess et al. |
| 2013/0008937 A1 | 1/2013 | Viola |
| 2013/0012983 A1 | 1/2013 | Kleyman |
| 2013/0015231 A1 | 1/2013 | Kostrzewski |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037595 A1 | 2/2013 | Gupta et al. |
| 2013/0041406 A1 | 2/2013 | Bear et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0075447 A1 | 3/2013 | Weisenburgh, II et al. |
| 2013/0092717 A1 | 4/2013 | Marczyk et al. |
| 2013/0098964 A1 | 4/2013 | Smith et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | Racenet et al. |
| 2013/0112730 A1 | 5/2013 | Whitman et al. |
| 2013/0119109 A1 | 5/2013 | Farascioni et al. |
| 2013/0146641 A1 | 6/2013 | Shelton, IV et al. |
| 2013/0146642 A1 | 6/2013 | Shelton, IV et al. |
| 2013/0153636 A1 | 6/2013 | Shelton, IV et al. |
| 2013/0153641 A1 | 6/2013 | Shelton, IV et al. |
| 2013/0161374 A1 | 6/2013 | Swayze et al. |
| 2013/0175316 A1 | 7/2013 | Thompson et al. |
| 2013/0193188 A1 | 8/2013 | Shelton, IV et al. |
| 2013/0256380 A1 | 10/2013 | Schmid et al. |
| 2013/0277410 A1 | 10/2013 | Fernandez et al. |
| 2013/0334280 A1 | 12/2013 | Krehel et al. |
| 2014/0014704 A1 | 1/2014 | Onukuri et al. |
| 2014/0014707 A1 | 1/2014 | Onukuri et al. |
| 2014/0021242 A1 | 1/2014 | Hodgkinson et al. |
| 2014/0048580 A1 | 2/2014 | Merchant et al. |
| 2014/0061280 A1 | 3/2014 | Ingmanson et al. |
| 2014/0076955 A1 | 3/2014 | Lorenz |
| 2014/0151431 A1 | 6/2014 | Hodgkinson et al. |
| 2014/0166720 A1 | 6/2014 | Chowaniec et al. |
| 2014/0166721 A1 | 6/2014 | Stevenson et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175146 A1 | 6/2014 | Knodel |
| 2014/0175150 A1 | 6/2014 | Shelton, IV et al. |
| 2014/0203062 A1 | 7/2014 | Viola |
| 2014/0239036 A1 | 8/2014 | Zerkle et al. |
| 2014/0239037 A1 | 8/2014 | Boudreaux et al. |
| 2014/0239038 A1 | 8/2014 | Leimbach et al. |
| 2014/0239040 A1 | 8/2014 | Fanelli et al. |
| 2014/0239041 A1 | 8/2014 | Zerkle et al. |
| 2014/0239043 A1 | 8/2014 | Simms et al. |
| 2014/0239044 A1 | 8/2014 | Hoffman |
| 2014/0239047 A1 | 8/2014 | Hodgkinson et al. |
| 2014/0246471 A1 | 9/2014 | Jaworek et al. |
| 2014/0246472 A1 | 9/2014 | Kimsey et al. |
| 2014/0246475 A1 | 9/2014 | Hall et al. |
| 2014/0246478 A1 | 9/2014 | Baber et al. |
| 2014/0252062 A1 | 9/2014 | Mozdzierz |
| 2014/0252064 A1* | 9/2014 | Mozdzierz ....... A61B 17/07207 227/176.1 |
| 2014/0252065 A1 | 9/2014 | Hessler et al. |
| 2014/0263539 A1 | 9/2014 | Leimbach et al. |
| 2014/0263540 A1 | 9/2014 | Covach et al. |
| 2014/0263541 A1 | 9/2014 | Leimbach et al. |
| 2014/0263542 A1 | 9/2014 | Leimbach et al. |
| 2014/0263544 A1 | 9/2014 | Ranucci et al. |
| 2014/0263546 A1 | 9/2014 | Aranyi |
| 2014/0263550 A1 | 9/2014 | Aranyi et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263557 A1 | 9/2014 | Schaller |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263570 A1 | 9/2014 | Hopkins et al. |
| 2014/0284371 A1 | 9/2014 | Morgan et al. |
| 2014/0291379 A1 | 10/2014 | Schellin et al. |
| 2014/0291380 A1 | 10/2014 | Weaner et al. |
| 2014/0291383 A1 | 10/2014 | Spivey et al. |
| 2014/0303668 A1 | 10/2014 | Nicholas et al. |
| 2014/0309665 A1 | 10/2014 | Parihar et al. |
| 2014/0332578 A1 | 11/2014 | Fernandez et al. |
| 2014/0339286 A1 | 11/2014 | Motooka et al. |
| 2014/0353358 A1 | 12/2014 | Shelton, IV et al. |
| 2014/0367445 A1 | 12/2014 | Ingmanson et al. |
| 2014/0367446 A1 | 12/2014 | Ingmanson et al. |
| 2015/0048143 A1 | 2/2015 | Scheib et al. |
| 2015/0053740 A1 | 2/2015 | Shelton, IV |
| 2015/0053742 A1 | 2/2015 | Shelton, IV et al. |
| 2015/0053744 A1 | 2/2015 | Swayze et al. |
| 2015/0060517 A1 | 3/2015 | Williams |
| 2015/0076205 A1 | 3/2015 | Zergiebel |
| 2015/0076211 A1 | 3/2015 | Irka et al. |
| 2015/0080912 A1 | 3/2015 | Sapre |
| 2015/0133996 A1 | 5/2015 | Shelton, IV et al. |
| 2015/0134076 A1 | 5/2015 | Shelton, IV et al. |
| 2015/0150556 A1 | 6/2015 | McCuen |
| 2015/0157321 A1 | 6/2015 | Zergiebel et al. |
| 2015/0173744 A1 | 6/2015 | Shelton, IV et al. |
| 2015/0173745 A1 | 6/2015 | Baxter, III et al. |

(56) References Cited

U.S. PATENT DOCUMENTS

| | | |
|---|---|---|
| 2015/0173746 A1 | 6/2015 | Baxter, III et al. |
| 2015/0173747 A1 | 6/2015 | Baxter, III et al. |
| 2015/0173748 A1 | 6/2015 | Marczyk et al. |
| 2015/0173749 A1 | 6/2015 | Shelton, IV et al. |
| 2015/0173750 A1 | 6/2015 | Shelton, IV et al. |
| 2015/0173755 A1 | 6/2015 | Baxter, III et al. |
| 2015/0173756 A1* | 6/2015 | Baxter, III ............ A61B 17/064 227/177.1 |
| 2015/0173760 A1 | 6/2015 | Shelton, IV et al. |
| 2015/0173761 A1 | 6/2015 | Shelton, IV et al. |
| 2015/0209040 A1 | 7/2015 | Whitman et al. |
| 2015/0250474 A1 | 9/2015 | Abbott et al. |
| 2015/0272557 A1 | 10/2015 | Overmyer et al. |
| 2015/0297222 A1 | 10/2015 | Huitema et al. |
| 2015/0297225 A1 | 10/2015 | Huitema et al. |
| 2015/0316431 A1 | 11/2015 | Collins et al. |
| 2015/0351765 A1 | 12/2015 | Valentine et al. |
| 2015/0359534 A1 | 12/2015 | Gibbons, Jr. |
| 2015/0366560 A1 | 12/2015 | Chen et al. |
| 2015/0374371 A1 | 12/2015 | Richard et al. |
| 2015/0374372 A1 | 12/2015 | Zergiebel et al. |
| 2015/0374376 A1 | 12/2015 | Shelton, IV |
| 2016/0030040 A1 | 2/2016 | Calderoni et al. |
| 2016/0051259 A1 | 2/2016 | Hopkins et al. |
| 2016/0058441 A1* | 3/2016 | Morgan ............ A61B 17/0644 606/219 |
| 2016/0058443 A1 | 3/2016 | Yates et al. |
| 2016/0066907 A1 | 3/2016 | Cheney et al. |
| 2016/0067074 A1 | 3/2016 | Thompson et al. |
| 2016/0089137 A1 | 3/2016 | Hess et al. |
| 2016/0095585 A1 | 4/2016 | Zergiebel et al. |
| 2016/0100835 A1 | 4/2016 | Linder et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |
| 2016/0120542 A1 | 5/2016 | Westling et al. |
| 2016/0166249 A1 | 6/2016 | Knodel |
| 2016/0166253 A1 | 6/2016 | Knodel |
| 2016/0199064 A1 | 7/2016 | Shelton, IV et al. |
| 2016/0199084 A1 | 7/2016 | Takei |
| 2016/0206336 A1 | 7/2016 | Frushour |
| 2016/0235494 A1 | 8/2016 | Shelton, IV et al. |
| 2016/0242773 A1 | 8/2016 | Sadowski et al. |
| 2016/0242774 A1 | 8/2016 | Ebner |
| 2016/0242779 A1 | 8/2016 | Aranyi et al. |
| 2016/0249915 A1 | 9/2016 | Beckman et al. |
| 2016/0249916 A1 | 9/2016 | Shelton, IV et al. |
| 2016/0249918 A1 | 9/2016 | Shelton, IV et al. |
| 2016/0249927 A1 | 9/2016 | Beckman et al. |
| 2016/0249929 A1 | 9/2016 | Cappola et al. |
| 2016/0249945 A1 | 9/2016 | Shelton, IV et al. |
| 2016/0256071 A1 | 9/2016 | Shelton, IV et al. |
| 2016/0256152 A1 | 9/2016 | Kostrzewski |
| 2016/0256154 A1 | 9/2016 | Shelton, IV et al. |
| 2016/0256160 A1 | 9/2016 | Shelton, IV et al. |
| 2016/0256161 A1 | 9/2016 | Dvermyer et al. |
| 2016/0256162 A1 | 9/2016 | Shelton, IV et al. |
| 2016/0256163 A1 | 9/2016 | Shelton, IV et al. |
| 2016/0256184 A1 | 9/2016 | Shelton, IV et al. |
| 2016/0256185 A1 | 9/2016 | Shelton, IV et al. |
| 2016/0256187 A1 | 9/2016 | Shelton, IV et al. |
| 2016/0262750 A1 | 9/2016 | Hausen et al. |
| 2016/0270783 A1 | 9/2016 | Yigit et al. |
| 2016/0270788 A1 | 9/2016 | Czernik |
| 2016/0278764 A1 | 9/2016 | Shelton, IV et al. |
| 2016/0278765 A1 | 9/2016 | Shelton, IV et al. |
| 2016/0278771 A1 | 9/2016 | Shelton, IV et al. |
| 2016/0278774 A1 | 9/2016 | Shelton, IV et al. |
| 2016/0278775 A1 | 9/2016 | Shelton, IV et al. |
| 2016/0278777 A1 | 9/2016 | Shelton, IV et al. |
| 2016/0278848 A1 | 9/2016 | Boudreaux et al. |
| 2016/0287250 A1 | 10/2016 | Shelton, IV et al. |
| 2016/0287251 A1 | 10/2016 | Shelton, IV et al. |
| 2016/0296216 A1 | 10/2016 | Nicholas et al. |
| 2016/0302791 A1 | 10/2016 | Schmitt |
| 2016/0310134 A1 | 10/2016 | Contini et al. |
| 2016/0324514 A1 | 11/2016 | Srinivas et al. |
| 2016/0324518 A1 | 11/2016 | Nicholas et al. |
| 2016/0338703 A1 | 11/2016 | Scirica et al. |
| 2016/0345971 A1* | 12/2016 | Bucciaglia ........ A61B 17/07207 |
| 2016/0354176 A1 | 12/2016 | Schmitt |
| 2016/0374678 A1 | 12/2016 | Becerra et al. |
| 2017/0000483 A1 | 1/2017 | Motai et al. |
| 2017/0020525 A1 | 1/2017 | Shah |
| 2017/0095251 A1* | 4/2017 | Thompson .......... A61B 17/3468 |
| 2018/0168600 A1* | 6/2018 | Shelton, IV .......... A61B 90/03 |
| 2019/0099181 A1* | 4/2019 | Shelton, IV .......... A61B 90/03 |
| 2020/0345364 A1* | 11/2020 | Becerra ............ A61B 17/07207 |
| 2022/0160358 A1* | 5/2022 | Wixey .................. A61B 34/37 |
| 2022/0233192 A1* | 7/2022 | Williams ............. A61B 17/072 |

FOREIGN PATENT DOCUMENTS

| | | | |
|---|---|---|---|
| CA | 2884962 A1 | 11/2015 | |
| CN | 101116629 B | * 12/2012 | ............ A61B 17/00 |
| DE | 2744824 A1 | 4/1978 | |
| DE | 2903159 A1 | 7/1980 | |
| DE | 3114135 A1 | 10/1982 | |
| DE | 4213426 A1 | 10/1992 | |
| DE | 4300307 A1 | 7/1994 | |
| EP | 0041022 A1 | 12/1981 | |
| EP | 0136950 A2 | 4/1985 | |
| EP | 0140552 A2 | 5/1985 | |
| EP | 0156774 A2 | 10/1985 | |
| EP | 0213817 A1 | 3/1987 | |
| EP | 0216532 A1 | 4/1987 | |
| EP | 0220029 A1 | 4/1987 | |
| EP | 0273468 A2 | 7/1988 | |
| EP | 0324166 A2 | 7/1989 | |
| EP | 0324635 A1 | 7/1989 | |
| EP | 0324637 A1 | 7/1989 | |
| EP | 0324638 A1 | 7/1989 | |
| EP | 0365153 A1 | 4/1990 | |
| EP | 0369324 A1 | 5/1990 | |
| EP | 0373762 A1 | 6/1990 | |
| EP | 0380025 A2 | 8/1990 | |
| EP | 0399701 A1 | 11/1990 | |
| EP | 0449394 A2 | 10/1991 | |
| EP | 0484677 A1 | 5/1992 | |
| EP | 0489436 A1 | 6/1992 | |
| EP | 0503662 A1 | 9/1992 | |
| EP | 0514139 A2 | 11/1992 | |
| EP | 0536903 A2 | 4/1993 | |
| EP | 0537572 A2 | 4/1993 | |
| EP | 0539762 A1 | 5/1993 | |
| EP | 0545029 A1 | 6/1993 | |
| EP | 0552050 A2 | 7/1993 | |
| EP | 0552423 A2 | 7/1993 | |
| EP | 0579038 A1 | 1/1994 | |
| EP | 0589306 A2 | 3/1994 | |
| EP | 0591946 A1 | 4/1994 | |
| EP | 0592243 A2 | 4/1994 | |
| EP | 0593920 A1 | 4/1994 | |
| EP | 0598202 A1 | 5/1994 | |
| EP | 0598579 A1 | 5/1994 | |
| EP | 0600182 A2 | 6/1994 | |
| EP | 0621006 A1 | 10/1994 | |
| EP | 0621009 A1 | 10/1994 | |
| EP | 0656188 A2 | 6/1995 | |
| EP | 0666057 A2 | 8/1995 | |
| EP | 0705571 A1 | 4/1996 | |
| EP | 0760230 A1 | 3/1997 | |
| EP | 1952769 A2 | 8/2008 | |
| EP | 2090253 A2 | 8/2009 | |
| EP | 2090254 A1 | 8/2009 | |
| EP | 2583630 A2 | 4/2013 | |
| EP | 2586382 A2 | 5/2013 | |
| EP | 2907456 A1 | 8/2015 | |
| EP | 3498182 A1 | 6/2019 | |
| FR | 391239 A | 10/1908 | |
| FR | 2542188 A1 | 9/1984 | |
| FR | 2660851 A1 | 10/1991 | |
| FR | 2681775 A1 | 4/1993 | |
| GB | 1352554 A | 5/1974 | |

(56) References Cited

FOREIGN PATENT DOCUMENTS

| | | |
|---|---|---|
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51149985 | 12/1976 |
| JP | 2001087272 | 4/2001 |
| SU | 659146 A1 | 4/1979 |
| SU | 728848 A1 | 4/1980 |
| SU | 980703 A1 | 12/1982 |
| SU | 990220 A1 | 1/1983 |
| WO | 2008302247 | 7/1983 |
| WO | 8910094 A1 | 11/1989 |
| WO | 9210976 A1 | 7/1992 |
| WO | 9308754 A1 | 5/1993 |
| WO | 9314706 A1 | 8/1993 |
| WO | 2004032760 A2 | 4/2004 |
| WO | 2009071070 A2 | 6/2009 |
| WO | 20150191887 A1 | 12/2015 |

OTHER PUBLICATIONS

G. Ramm and A.I. Katsevich, The Radon Transform and Local Tomography, CRC Press, 1996.
F. Natterer, The Mathematics of Computerized Tomography, Wiley, 1989.
G.T. Herman et al., Basic Methods of Tomography and Inverse Problems, Hildger, 1987.
G.T. Herman and Attila Kuba, Discrete Tomography, Birhauser, 1999.

\* cited by examiner

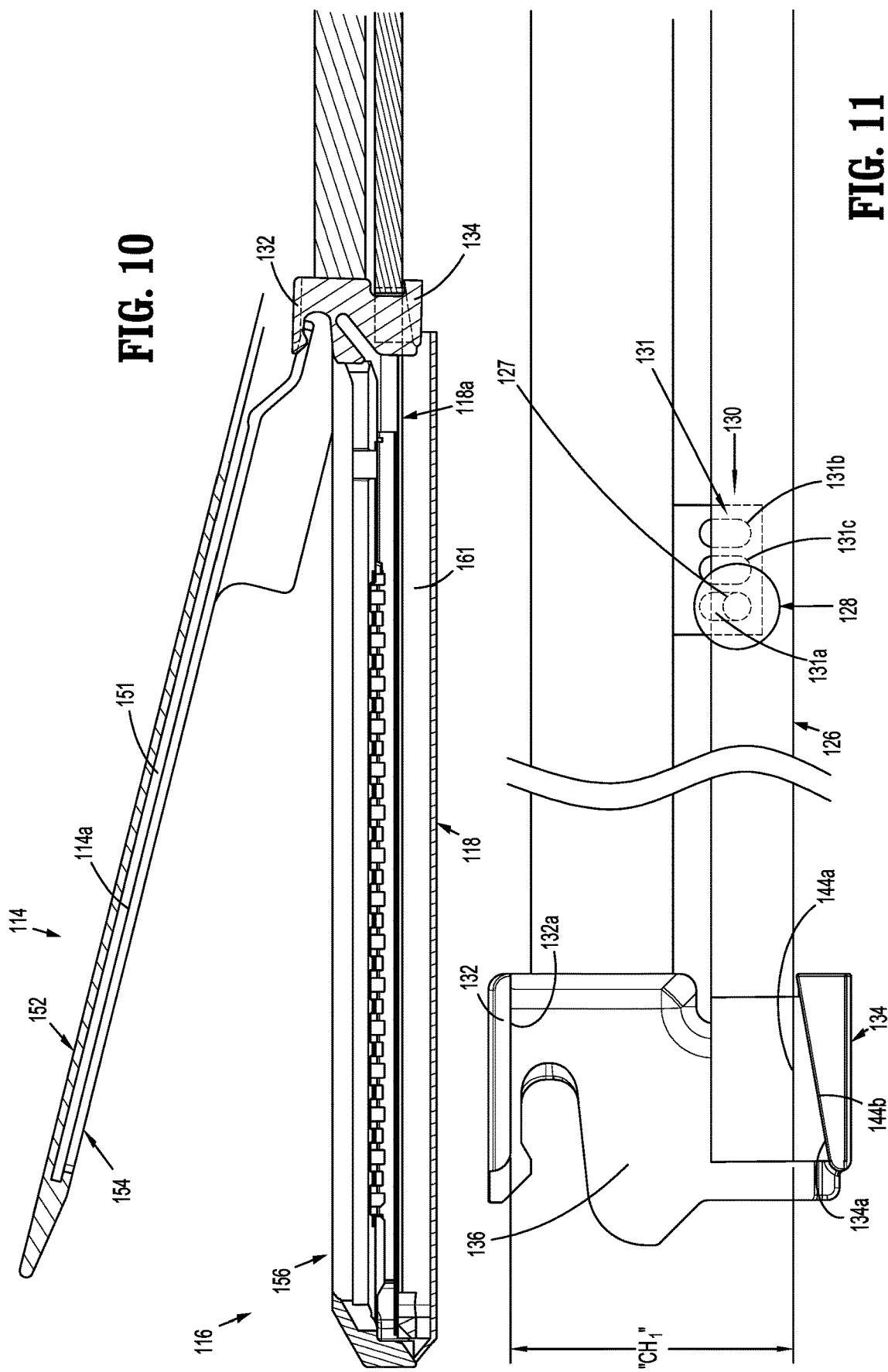

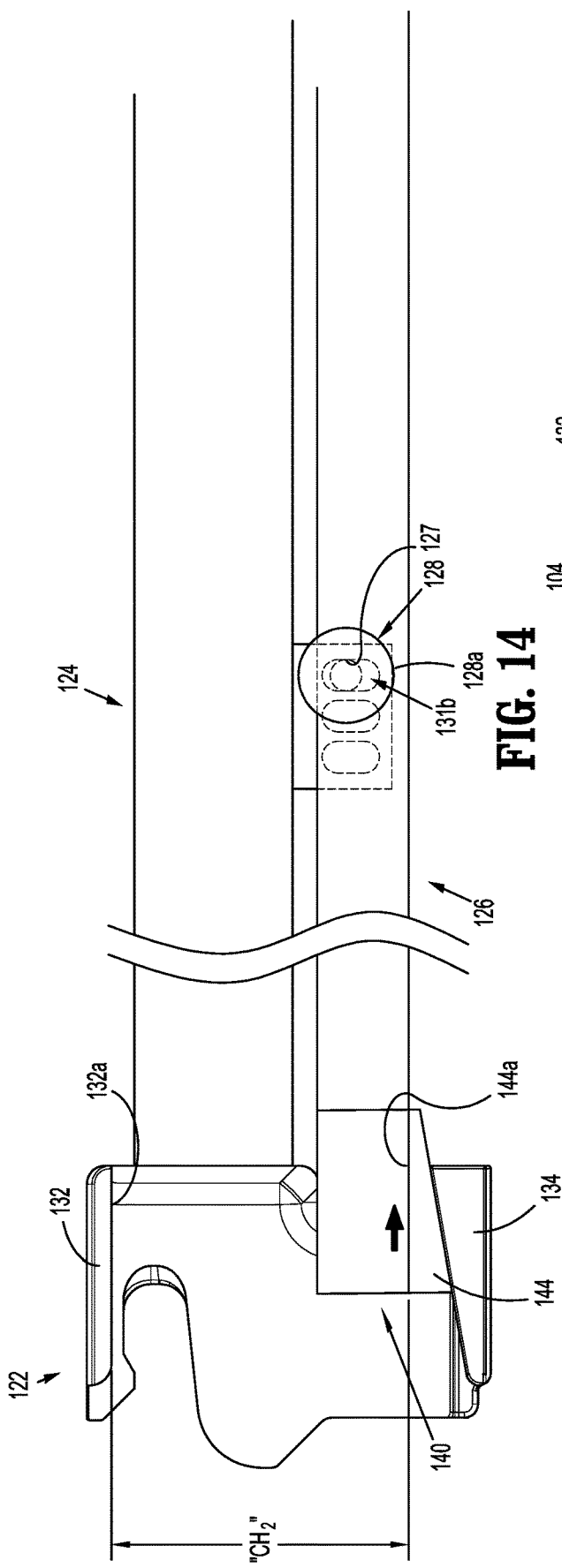
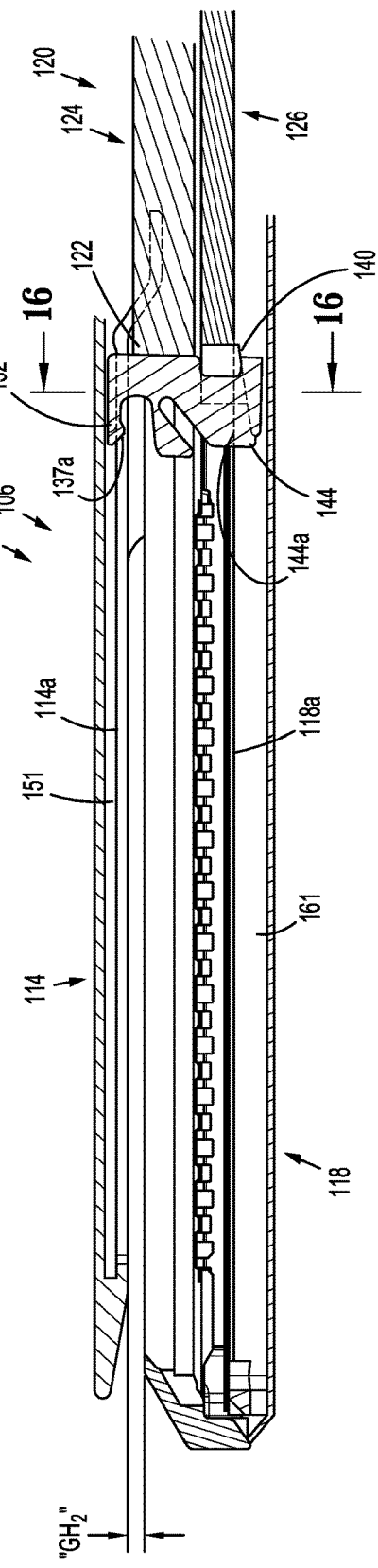
FIG. 14
FIG. 15

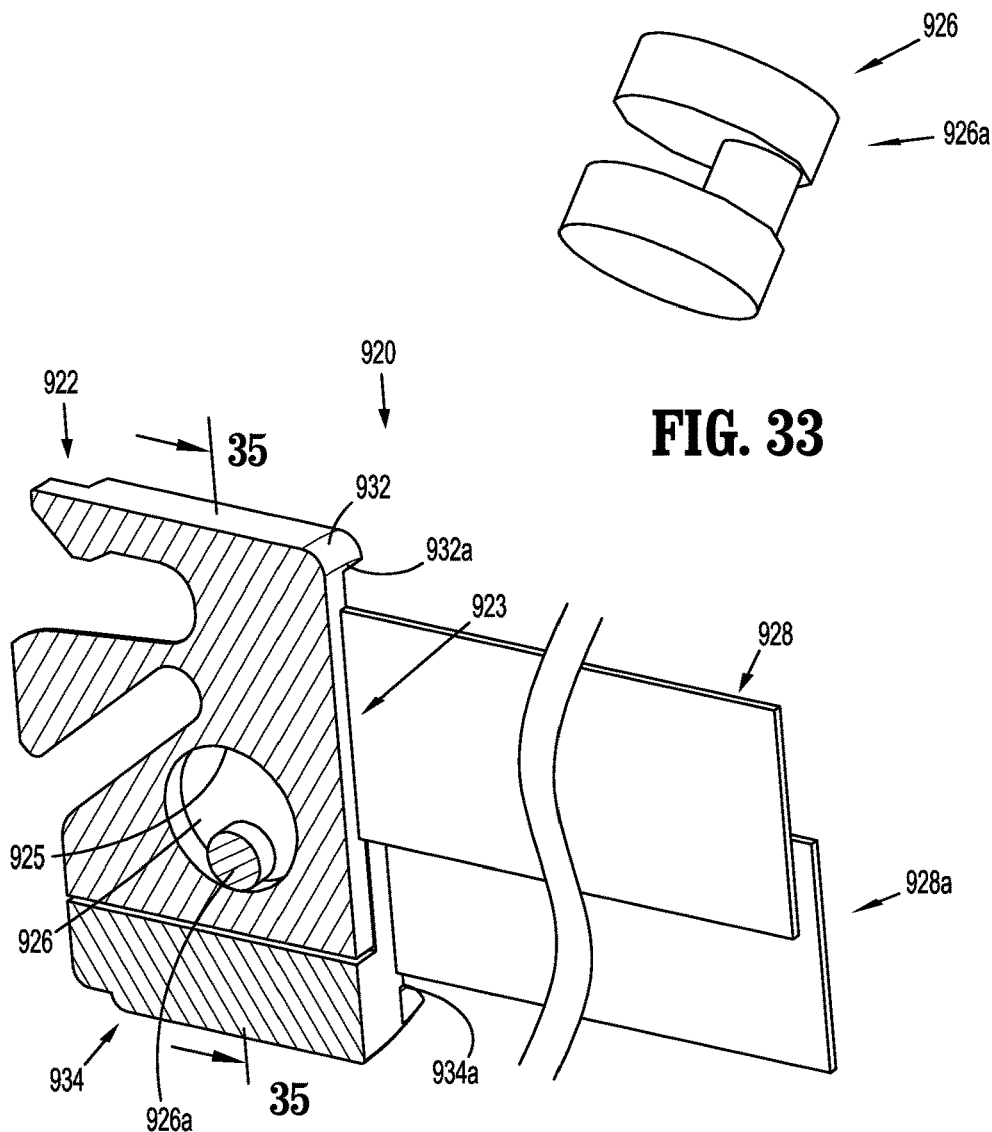
FIG. 33
FIG. 34
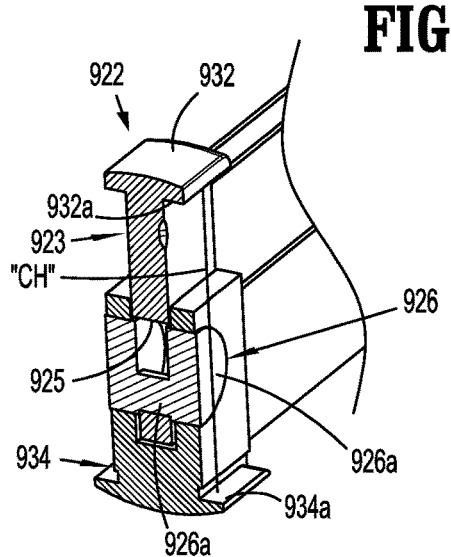
FIG. 35

SURGICAL STAPLING APPARATUS WITH ADJUSTABLE HEIGHT CLAMPING MEMBER

FIELD

This disclosure relates to surgical stapling devices having a clamping member for setting a tissue gap. More particularly, this disclosure relates to surgical stapling devices having a clamping member with an adjustable height for adjusting a tissue gap.

BACKGROUND

Surgical stapling devices for stapling tissue are well known in the art and typically include a handle assembly, a body portion extending distally from the handle assembly, and a tool assembly supported on a distal end of the body portion. The tool assembly includes first and second jaws which are movable in relation to each other between open and closed or approximated positions. The first jaw includes an anvil assembly and the second jaw supports a cartridge which houses a plurality of staples. The cartridge can also include a knife for severing tissue. In known devices, the stapling apparatus includes a clamping member that is engaged with the first and second jaws and is movable along the first and second jaws to set a tissue gap between the anvil assembly and the cartridge during a stapling procedure. However, the size of the tissue gap appropriate for a surgical procedure depends on the thickness of the tissue being treated which will change from procedure to procedure, and may change along the length of the first and second jaws.

A continuing need exists in the art for a surgical stapling device capable of changing the size of the tissue gap set by the clamping member to accommodate tissues of varying thickness.

SUMMARY

A surgical stapling device includes a body portion, a tool assembly, and a drive assembly. The body portion defines a longitudinal axis and has a proximal portion and a distal portion. The tool assembly is supported on the distal portion of the body portion. The tool assembly includes an anvil assembly, a channel member pivotally supported relative to the anvil assembly, and a staple cartridge releasably disposed within the channel member. The tool assembly is movable from an open position to an approximated position. The staple cartridge supports a plurality of staples and includes an actuation sled that is movable between a retracted position and an advanced position to eject the plurality of staples from the staple cartridge. The drive assembly is movably supported within the tool assembly from a retracted position to an advanced position to move the tool assembly from the open position to the approximated position and to maintain the tool assembly in the approximated position. The drive assembly includes a clamping member and an adjustment member. The clamping member includes a first clamping surface configured to engage the anvil assembly. The adjustment member includes a second clamping surface configured to engage the staple cartridge. The first clamping surface is spaced from the second clamping surface to define a clamping height. The adjustment member is moveable relative to the clamping member between a first position and a second position to change the clamping height.

In certain aspects of the disclosure, the first position of the adjustment member is longitudinally spaced from the second position of the adjustment member. The first position of the adjustment member may be vertically spaced from the second position of the adjustment member. The channel member may define a slot and the adjustment member may include a flange. The flange may be receivable within the slot of the channel member. The anvil assembly may define a slot and the clamping member may include a pair of flanges. The pair of flanges of the clamping member may be receivable within the slot of the anvil assembly.

In some aspects of the disclosure, the drive assembly includes a drive beam and a securement mechanism for securing the adjustment member relative to the drive beam. The securement member may include an adjustment knob and a thread screw extending from the adjustment knob. Movement of the drive assembly beyond the partially advanced position may move the actuation sled from a retracted position to an advanced position to eject the plurality of staples from the staple cartridge. The clamping member may include an upper flange and a lower flange interconnected by a vertical strut. The clamping member may be positioned to engage the actuation sled to move the actuation sled distally within the staple cartridge as the drive assembly moves from the retracted position towards a fully advanced position. The adjustment member may include an inclined surface and the clamping member may include an inclined surface. Movement of the adjustment member relative to the clamping member may slide the inclined surfaces relative to each other.

A drive assembly for a surgical stapling assembly includes a clamping member, a drive beam extending from the clamping member, and an adjustment member. The clamping member includes an upper flange portion and a vertical strut. The upper flange includes a first clamping surface configured to engage an anvil assembly. The drive beam extends from the clamping member and is configured for operable engagement with an actuation mechanism. The adjustment member is disposed relative to the clamping member and includes a second clamping surface configured to engage a staple cartridge. The first clamping surface is spaced from the second clamping surface to define a clamping height. The adjustment member is moveable relative to the clamping member between a first position and a second position to change the clamping height.

In certain aspects of the disclosure, the upper flange portion is configured to be received within a slot of the anvil assembly. The adjustment member may include a flange portion configured to be received within a slot of a staple cartridge. The drive assembly may further include a securement mechanism for securing the drive beam relative to the adjustment mechanism. The securement mechanism may be a threaded screw. The first position of the adjustment member may be longitudinally spaced from the second position of the adjustment member. The first position of the adjustment member may be vertically spaced from the second position of the adjustment member.

BRIEF DESCRIPTION OF THE DRAWINGS

Various aspects of the disclosure are described herein with reference to the drawings, wherein:

FIG. 10 is an enlarged, side, cross-sectional view of the tool assembly shown in FIG. 2 in the open position with the drive assembly in a first configuration and in a retracted position;

FIG. 11 is a side perspective view of the drive assembly shown in FIG. 4 in the first configuration;

FIG. 14 is a side view of the drive assembly in a second configuration;

FIG. 15 is a side, cross-sectional view of the tool assembly shown in FIG. 10 in a closed position with the drive assembly in the second configuration and in a partially advanced position;

FIG. 33 is a top, perspective view of a cam member of the drive assembly shown in FIG. 32;

FIG. 34 is a side cross-sectional view taken along section line 34-34 shown in FIG. 32; and FIG. 35 is an end, cross-sectional view taken along section line 35-35 shown in FIG. 34.

DETAILED DESCRIPTION

Figure 1:
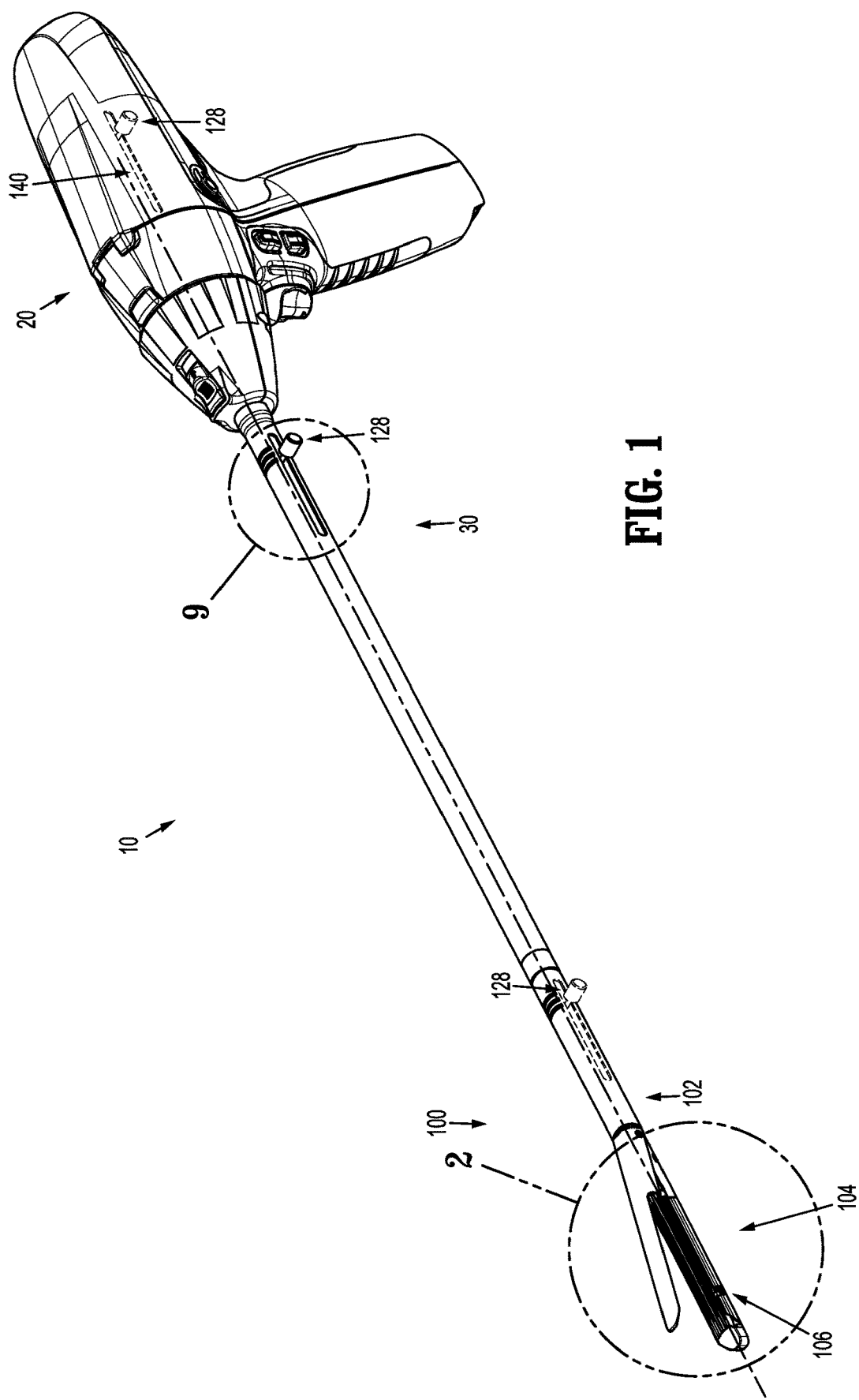
FIG. 1 is a side, perspective view of a powered surgical stapling device including a loading unit having a tool assembly in an open position according to aspects of the disclosure.

The disclosed surgical stapling device will now be described in detail with reference to the drawings in which like reference numerals designate identical or corresponding elements in each of the several views. However, it is to be understood that the disclosed aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel.

The disclosed surgical stapling device includes a drive assembly having a dynamic clamping member that is configured with an adjustable clamp height for adjusting a maximum tissue gap between tissue contact surfaces of anvil and cartridge assemblies of the stapling device.

FIG. 1 illustrates a surgical stapling device according to exemplary aspects of the disclosure, shown generally as stapling device 10. The stapling device 10 includes a powered handle assembly 20, an adapter assembly 30 releasably secured to the powered handle assembly 20, and a loading unit 100 releasably secured to the adapter assembly 30. Although shown as individual or separable components, it is envisioned that any or all the powered handle assembly 20, adapter assembly 30, and loading unit 100 may be integrally formed.

Figure 4:
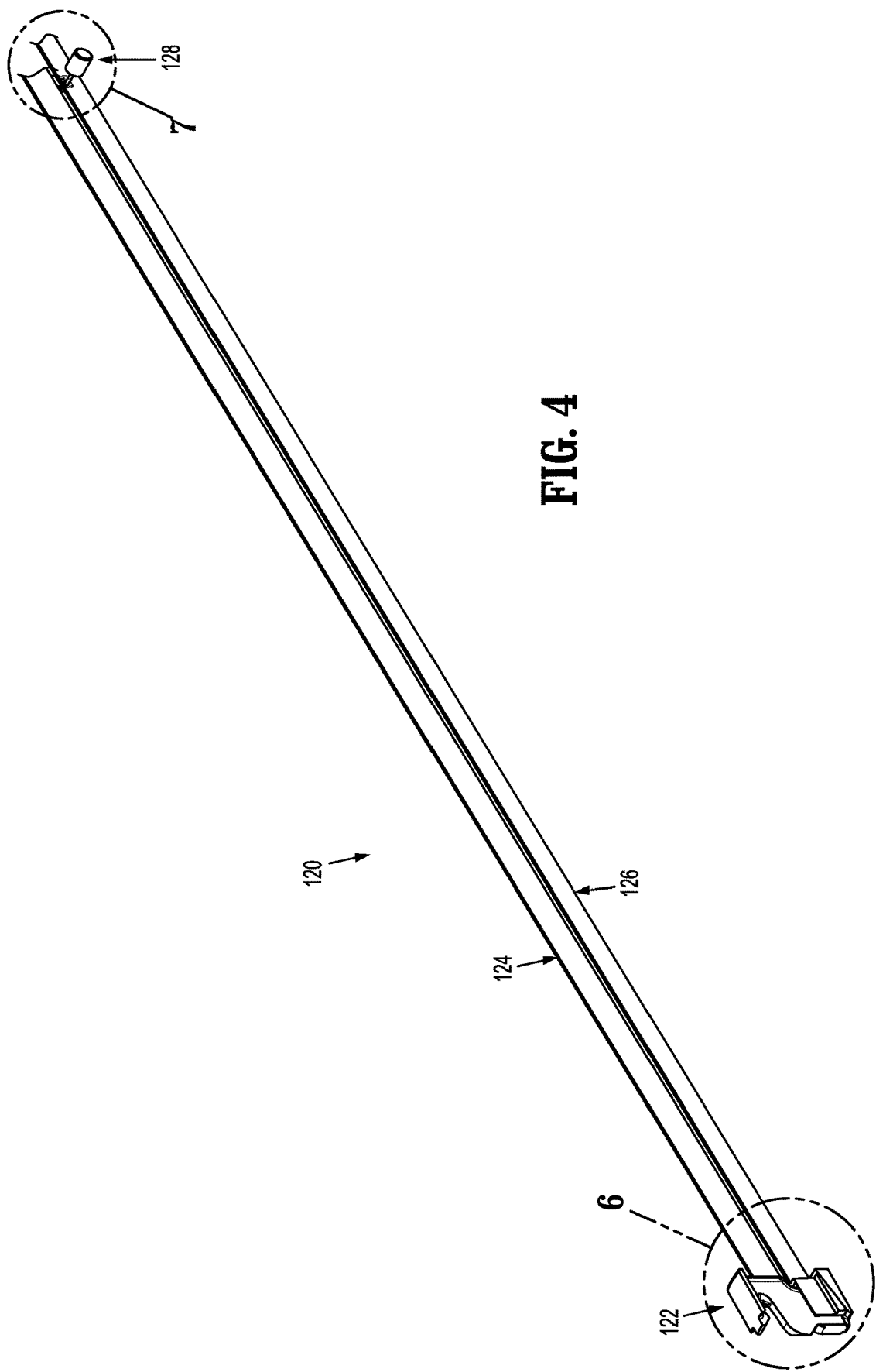
FIG. 4 is a side perspective view a drive assembly of the surgical stapling device shown in FIG. 1.
Figure 5:
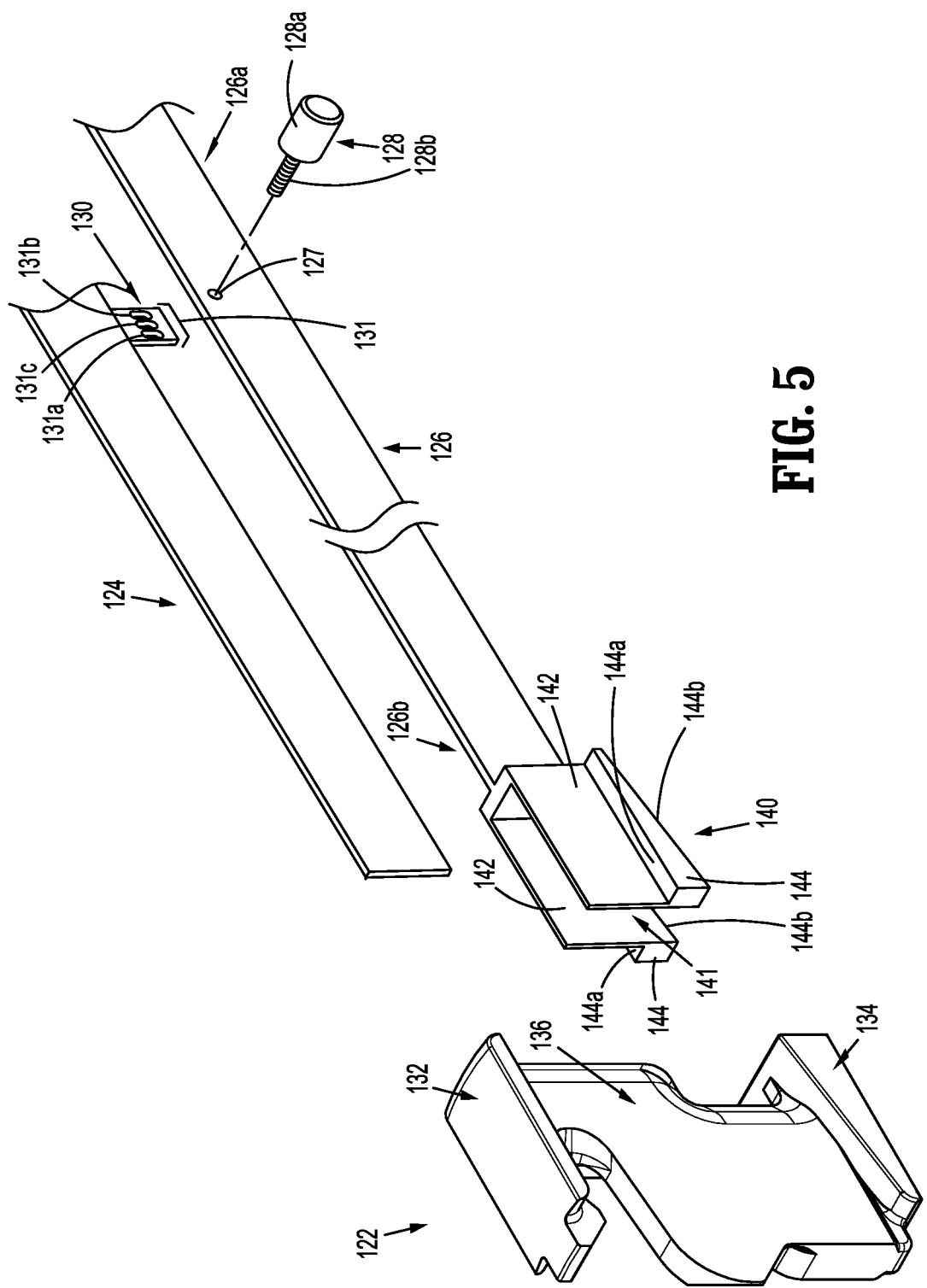
FIG. 5 is an enlarged, side perspective view with parts separated of the drive assembly shown in FIG. 4.
Figure 7:
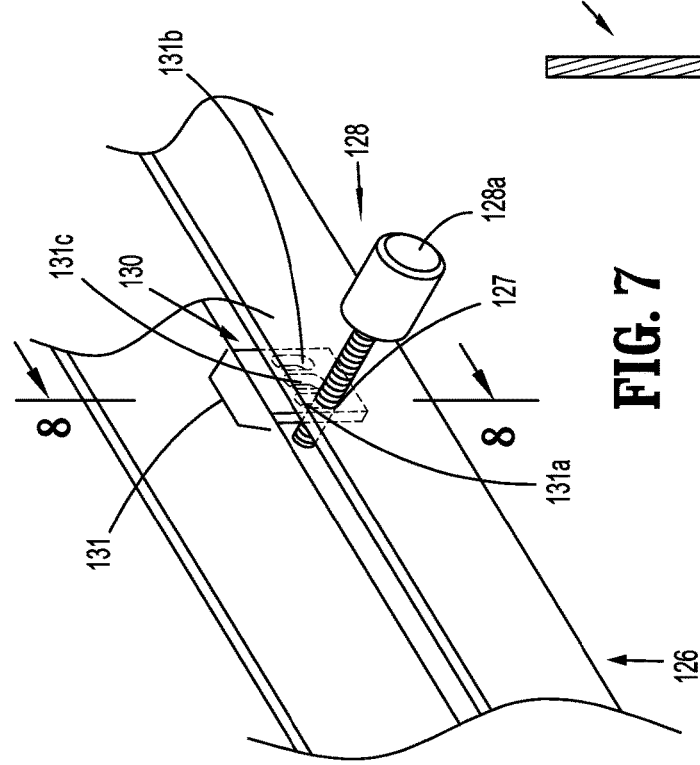
FIG. 7 is an enlarged, side perspective view of the indicated area of detail shown in FIG. 4.
Figure 8:
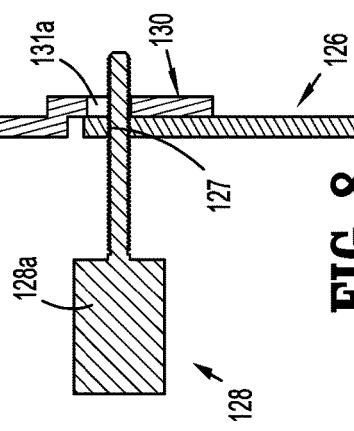
FIG. 8 is a cross-sectional view taken along section line 8-8 shown in FIG. 7.

As will be described in further detail below, the surgical stapling device 10 includes an adjustment mechanism 128 that is engaged with a drive assembly 120 (FIG. 4) of the surgical stapling device 10. As shown, the adjustment mechanism 128 may include an adjustment knob 128a that is supported on the adapter assembly 30, the loading unit 100, or the powered handle assembly 20.

Figure 2:
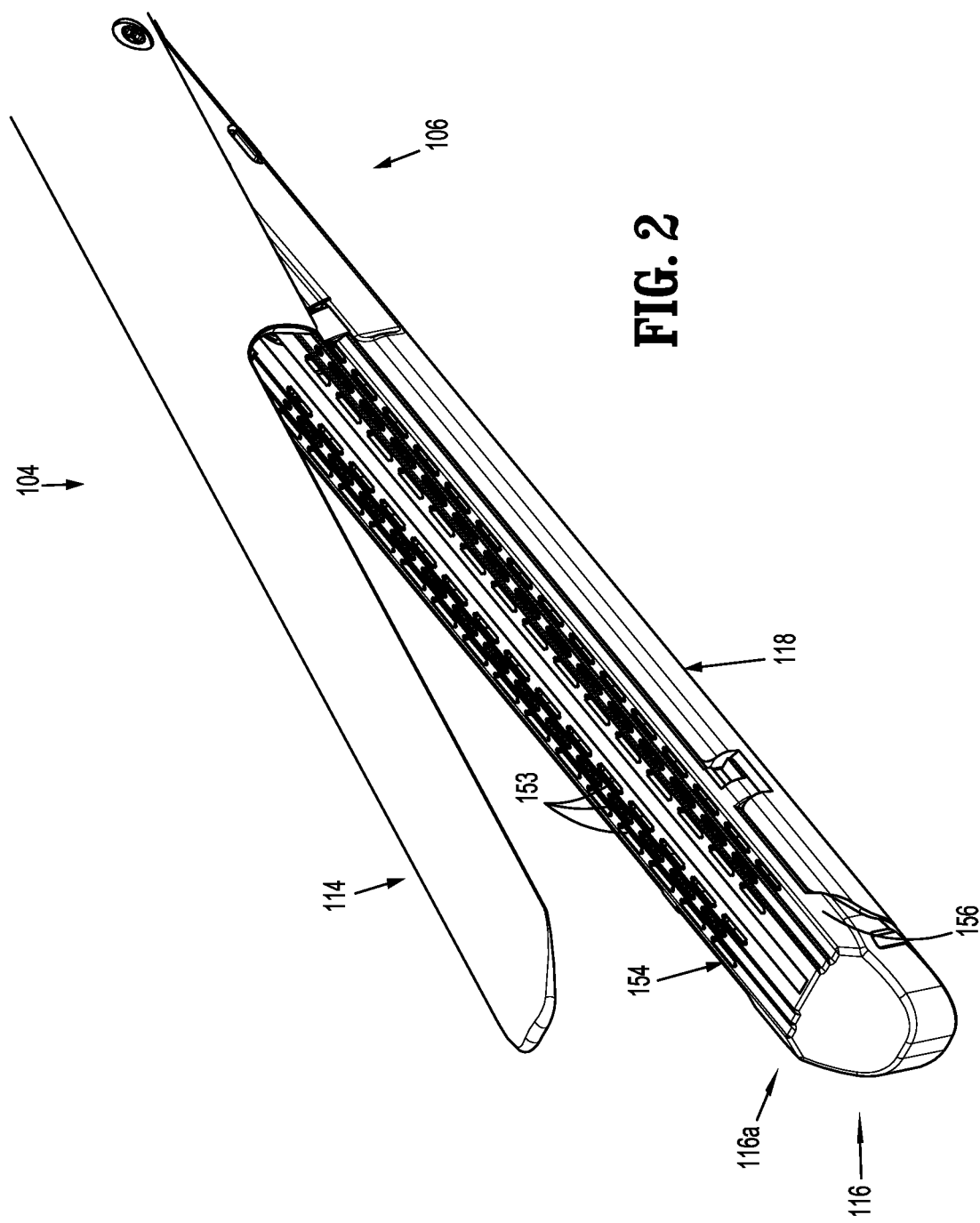
FIG. 2 is a side, perspective view of the indicated area of detail shown in FIG. 1.
Figure 3:
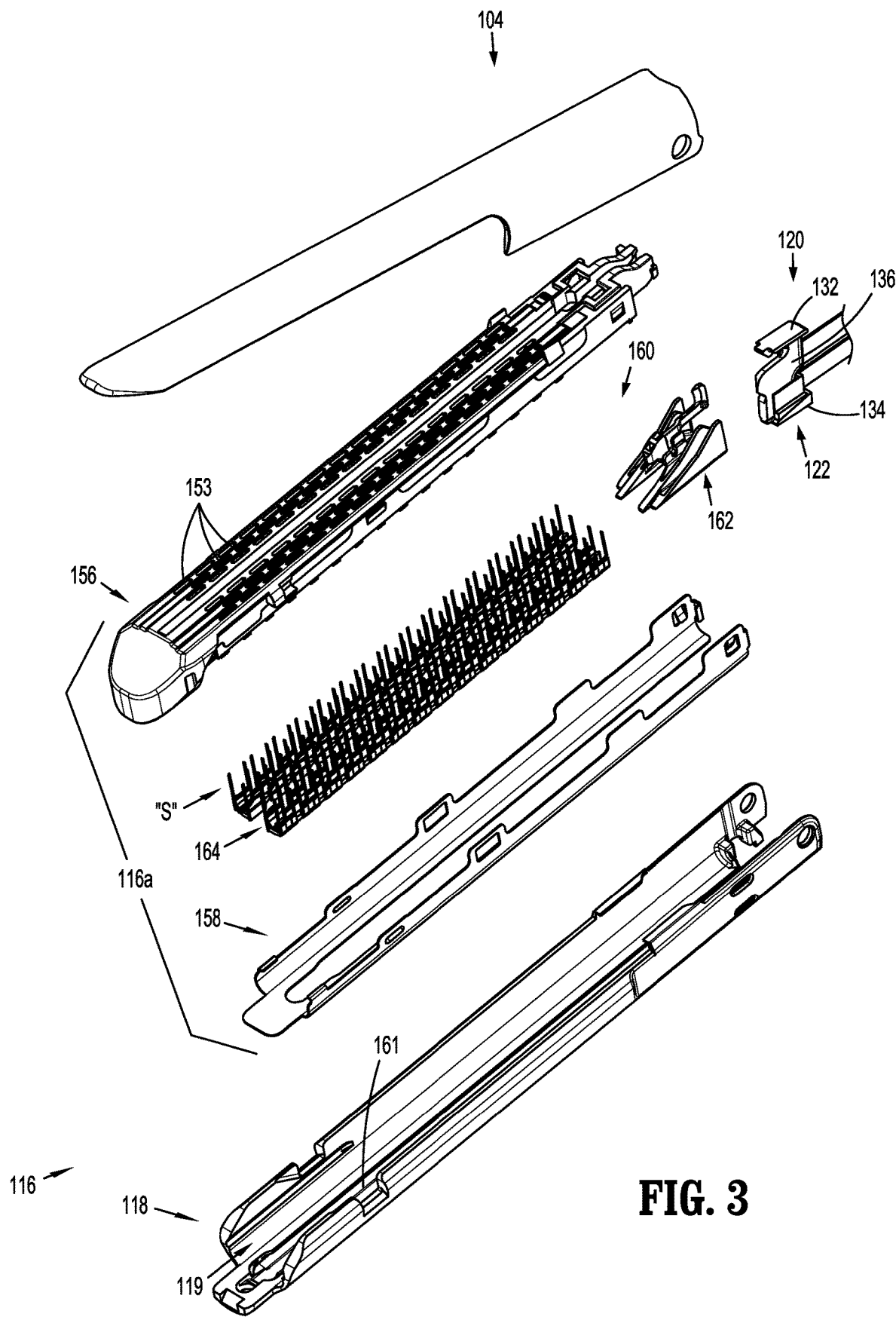
FIG. 3 is side perspective view with parts separated of the loading unit shown in FIGS. 1 and 2.
Figure 12:
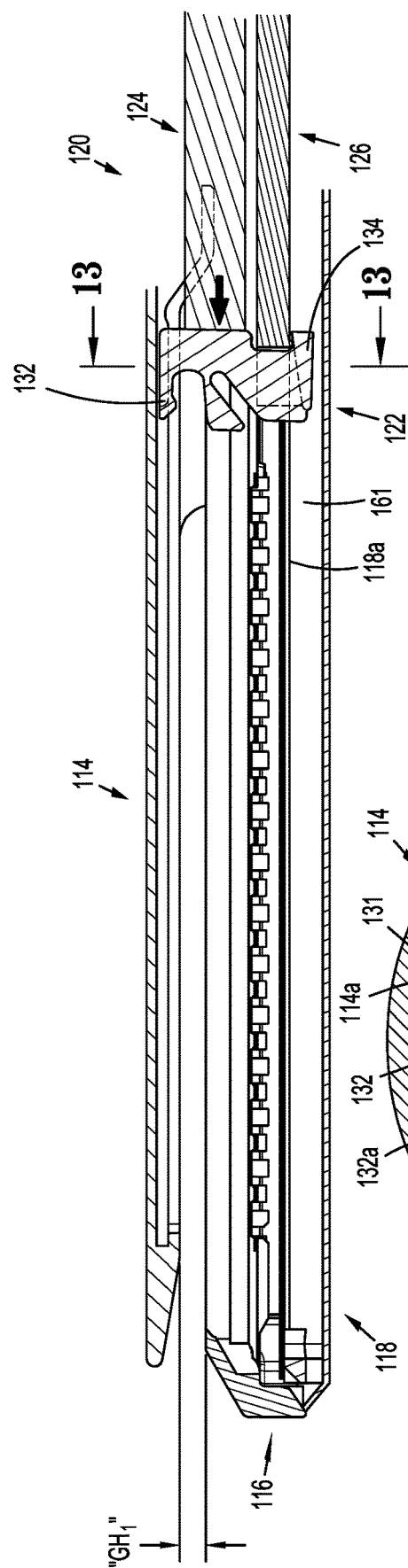
FIG. 12 is a side perspective view of the tool assembly shown in FIG. 10 in a closed position with the drive assembly in the first configuration and in a partially advanced position.

FIGS. 2 and 3 illustrate the tool assembly 104 of the loading unit 100 of the surgical stapling device 10. The tool assembly 104 is pivotally secured to a body portion 102 (FIG. 1) of the loading unit 100 and includes a jaw assembly 106 having an anvil assembly 114 and a cartridge assembly 116. The cartridge assembly 116 includes a channel member 118, and a staple cartridge 116a that is received within the channel member 118. The anvil assembly 114 and cartridge assembly 116 are pivotable relative to each other between an open position (FIG. 10) and an approximated or clamped position (FIG. 12). A drive assembly 120 (FIG. 4) extends from the body portion 102 of the loading unit 100 into the tool assembly 104 and is translatable through the tool assembly 104 to cause actuation of the jaw assembly 106 to fire staples "S" from the staple cartridge 116a.

The loading unit 100 is substantially as described in U.S. Pat. No. 9,016,539 ("the '539 patent"). Accordingly, the components of the loading unit 100 which are common to that which is disclosed in the '539 patent will only be described herein to the extent necessary to fully disclose the aspects of the drive assembly 120 and its method of operation.

The anvil assembly 114 of the jaw assembly 106 of the tool assembly 104 defines a channel 151 (FIG. 10) and includes an inner clamping surface 114a. In certain aspects of the disclosure, the anvil assembly 114 includes an anvil body 150 and an anvil plate 152 (FIG. 10) secured to the underside of the anvil body 150 to form the channel 151. The anvil plate 152 defines plurality of staple receiving depressions (not shown).

The staple cartridge 116a of the jaw assembly 106 includes a cartridge body 156 supported in a cartridge holder 158, a plurality of staples "S", and a staple firing assembly 160. The staple firing assembly 160 includes an actuation sled 162 (FIG. 3) and a plurality of pusher members 164 (FIG. 3). The channel member 118 defines a cavity 119 (FIG. 3) that receives the staple cartridge 116a. More specifically, the cartridge body 156 of the staple cartridge 116a is secured within the cavity 119 of the channel member 118 with, e.g., a snap-fit connection. Other forms of connections are contemplated and may be used in place of the snap-fit connection, or in addition thereto, to fixedly or releasably secure the cartridge assembly 116 within the cavity 119 of the channel member 118.

The channel member 118 is pivotally secured to the anvil assembly 114, and includes an inner clamping surface 118a (FIG. 10) defining a channel or slot 161. The cartridge body 156 defines a plurality of laterally spaced staple retention slots 153 which are positioned in alignment with the staple receiving depressions (not shown) in the anvil plate 152 (FIG. 10) of the anvil assembly 114 when the jaw assembly 106 is in the clamped position. Each retention slot 153 is configured to receive a fastener or staple "S" and a pusher 164. The actuation sled 162 is positioned within the cartridge body 156 of the cartridge assembly 116 and is configured to pass longitudinally through the cartridge body 156 into engagement with the pushers 164 to lift the pushers within the cartridge body 156 and sequentially eject the staples "S" from the cartridge body 156. The actuation sled 162 supports a knife mechanism 166 that includes a knife that is cammed into a cutting position when the actuation sled 162 is engaged by the dynamic clamping member 122.

FIGS. 4-7 illustrate the drive assembly 120 of the stapling device 10 (FIG. 1) which includes a dynamic clamping member 122, a drive beam 124, an adjustment beam 126, and a securement mechanism 128. The drive beam 124 defines a longitudinal axis and extends proximally from the dynamic clamping member 122 into the body portion 102 of the loading unit 100. The adjustment beam 126 extends along a length of the drive beam 124 and is selectively securable to the drive beam 124 by the securement mechanism 128. A proximal end of the drive beam 124 is configured to engage a drive member (not shown) of the adapter assembly 30 and/or the powered handle assembly 20 for advancing and retracting the drive assembly 120 within the adapter assembly 30 and the tool assembly 104. A tab 130 (FIG. 5) is disposed along the length of the drive beam 124 and defines a first opening 131a, a second opening 131b, a third opening 131c (collectively, openings 131). In aspects of the disclosure, each of the openings 131 are oblong in a direction transverse to the longitudinal axis of the drive beam 124 to accommodate transverse movement of the adjustment beam 126 relative to the drive beam 124 as the adjustment beam 126 is moved longitudinally relative to the drive beam 124. Although shown to include three openings 131, it is envisioned that the drive beam 124 may include only two openings or may include more than three openings. Although the tab 130 is shown formed on the drive beam 124, it is envisioned that the tab 130 may instead be formed on the adjustment beam 126. As will be described in detail below, the adjustment beam 126 and the securement mechanism 128 operate as a mechanism for adjusting a clamping height "CH" (FIG. 6) of the dynamic clamping member 122.

In certain aspects of the disclosure, the drive beam 124 and/or the adjustment beam 126 of the drive assembly 120 is formed from a plurality of stacked sheets that are formed of a resilient or flexible material, e.g., stainless steel.

The dynamic clamping member 122 of the drive assembly 120 includes an upper flange portion 132, a lower flange portion 134, and a vertical strut 136 interconnecting the upper flange portion 132 and the lower flange portion 134. The upper flange portion 132 is sized and dimensioned to be slidably received within the channel 151 (FIG. 10) of the anvil assembly 114 and includes a clamping surface 132a (FIG. 13) that engages the inner clamping surface 114a (FIG. 13) of the anvil assembly 114 to cause pivoting of the cartridge assembly 116 relative to the anvil assembly 114 to move the jaw assembly 106 from the open position to the clamped position. The lower flange portion 134 is sized and dimensioned to be slidably received within the channel 161 (FIG. 13) of the channel member 118 and includes inclined surfaces 134a facing the upper flange portion 132 of the dynamic clamping member 122.

The adjustment beam 126 of the drive assembly 120 extends along a length of the drive beam 124. A proximal portion 126a of the adjustment beam 126 defines an opening 127 for receiving the securement mechanism 128. As shown, the securement mechanism 128 includes the adjustment knob 128a and a threaded screw 128b, and the opening 127 is configured to securely receive the threaded screw 128b. Although shown as a threaded connection, it is envisioned that the adjustment beam 126 may be secured relative to the drive beam 124 in any suitable manner. The opening 127 in the adjustment beam 126 is positioned to align with any one of the openings 131 in the tab 130 of the drive beam 124.

Figure 6:
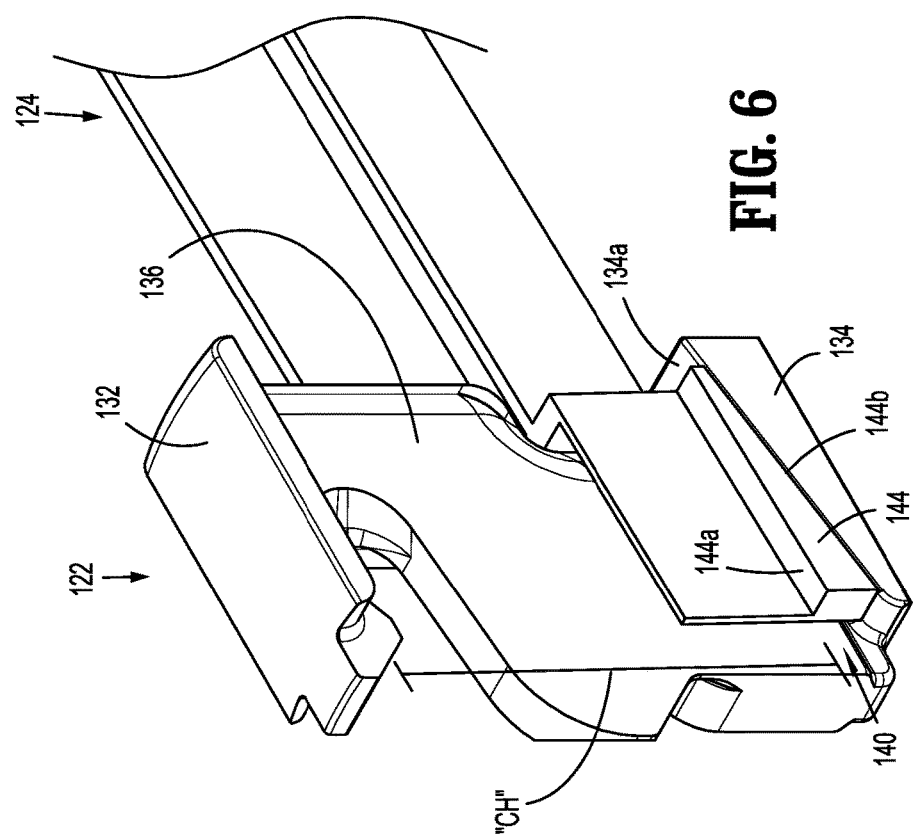
FIG. 6 is an enlarged, side perspective view of the indicated area of detail shown in FIG. 4.

An engagement portion 140 is formed on a distal end 126b of the adjustment beam 126 of the drive assembly 120. The engagement portion 140 of the adjustment beam 126 includes a pair of extensions 142 that are spaced apart from one another to form a slot 141 for receiving the vertical strut 136 of the dynamic clamping member 122. Each of the extensions 142 includes an adjustment flange 144 that is configured to be received within the channel 161 (FIG. 10) of the channel member 118 and includes a clamping surface 144a and an opposed inclined surface 144b. The clamping surfaces 144a of the adjustment flanges 144 are configured to engage the inner clamping surface 118a (FIG. 10) of the channel member 118. The engagement portion 140 of the adjustment beam 126 is configured such that when the vertical strut 136 of the dynamic clamping member 122 is received within the slot 141 of the engagement portion 140, the inclined surfaces 144b of the adjustment flanges 144 of the engagement portion 140 of the adjustment beam 126 engage the inclined surfaces 134a of the lower flange portion 134 of the dynamic clamping member 122. The distance between the clamping surface 132a of the of upper flange portion 132 of the dynamic clamping member 122 and the clamping surface 144a of the adjustment flange 144 of the engagement portion 140 of the adjustment beam 126 defines the clamping height "CH" (FIG. 6). As will be described in further detail below, by changing the longitudinal position of the adjustment beam 126 of the drive assembly 120 relative to the drive beam 124 of the drive assembly 120, the clamping height "CH" may be adjusted.

FIGS. 9-13 illustrate the drive assembly 120 of loading unit 100 of the stapling device 10 (FIG. 1) in a first configuration. In the first configuration, the adjustment beam 126 is longitudinally positioned relative to the drive beam 124 in its distal-most position such that the opening 127 in the adjustment beam 126 is aligned with the first opening 131a in the drive beam 124. When the adjustment beam 126 is in the distal-most position, the adjustment flanges 144 of the engagement portion 140 of the adjustment beam 126 are positioned relative to the lower flanges 134 of the dynamic clamping member 122 such that a first clamp height "H", i.e., the distance between the clamping surfaces 132a of the upper flange portion 132 of the dynamic clamping member 122 and the clamping surfaces 144a of the adjustment flanges 144, is greatest. In this manner, when the dynamic clamping member 122 is advanced, the anvil assembly 114 pivots relative to the cartridge assembly 116 to create a gap height "GH" between a tissue contacting surface 114b of the anvil assembly 114 and a tissue contacting surface 116b of the cartridge assembly 116 of the jaw assembly 106.

Figure 9:
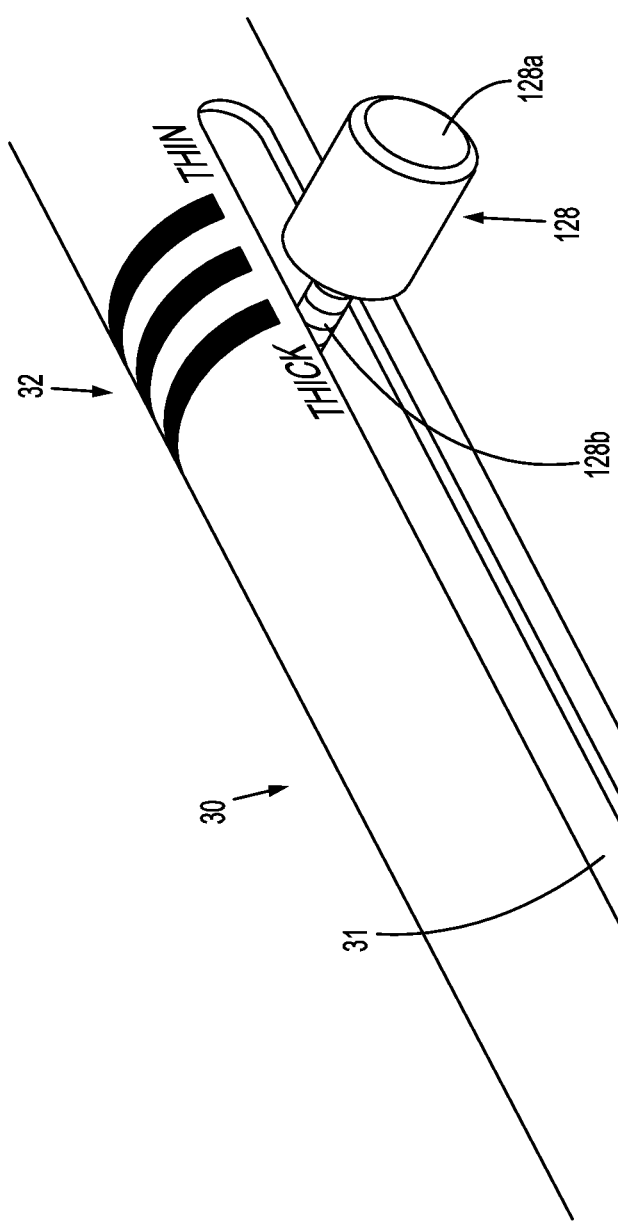
FIG. 9 is a side, perspective view of the indicated area of detail shown in FIG. 1.

FIG. 9 illustrates the securement mechanism 128 of the drive assembly 120 in the first position. As shown, the adapter assembly 30 defines a slot 31 along its length for accommodating movement of the securement mechanism 128 of the drive assembly 120 during operation of the stapling device 10. The adapter assembly 30 includes markings 32 along the slot 31 to indicate the position of the adjustment beam 126 relative to the drive beam 124 of the drive assembly 120. When drive assembly 120 is in a first configuration with the securement mechanism 128 in the first position, the securement mechanism 128 aligns with the distal-most marking of the markings 32 indicating that the stapling device 10 is configured to accommodate thick tissue.

FIG. 10 illustrates the jaw assembly 106 of the tool assembly 104 of the loading unit 100 of the stapling device 10 (FIG. 1) with the drive assembly 120 in the first configuration and in a retracted position. When the drive assembly 120 is in the retracted position, the anvil assembly 114 is spaced from the cartridge assembly 116, i.e., in the open position, to permit placement of tissue between the tissue contacting surfaces 114b, 116b of the respective anvil assembly 114 and cartridge assembly 116.

FIG. 11 illustrates the drive assembly 120 of the loading unit 100 in the first configuration with the adjustment beam 126 of the drive assembly 120 in its distal-most position relative to the drive beam 124 with the opening 127 in the adjustment beam 126 in alignment with the first opening 131a in the drive member 122. When the drive assembly 120 is in the first configuration, the distance between the clamping surface 132a of the upper flange portion 132 of the dynamic clamping member 122 and the clamping surface 144a of the adjustment flanges 144 of the engagement portion 140 of the adjustment beam 126 are spaced to define a first clamping height "CH1".

Figure 13:
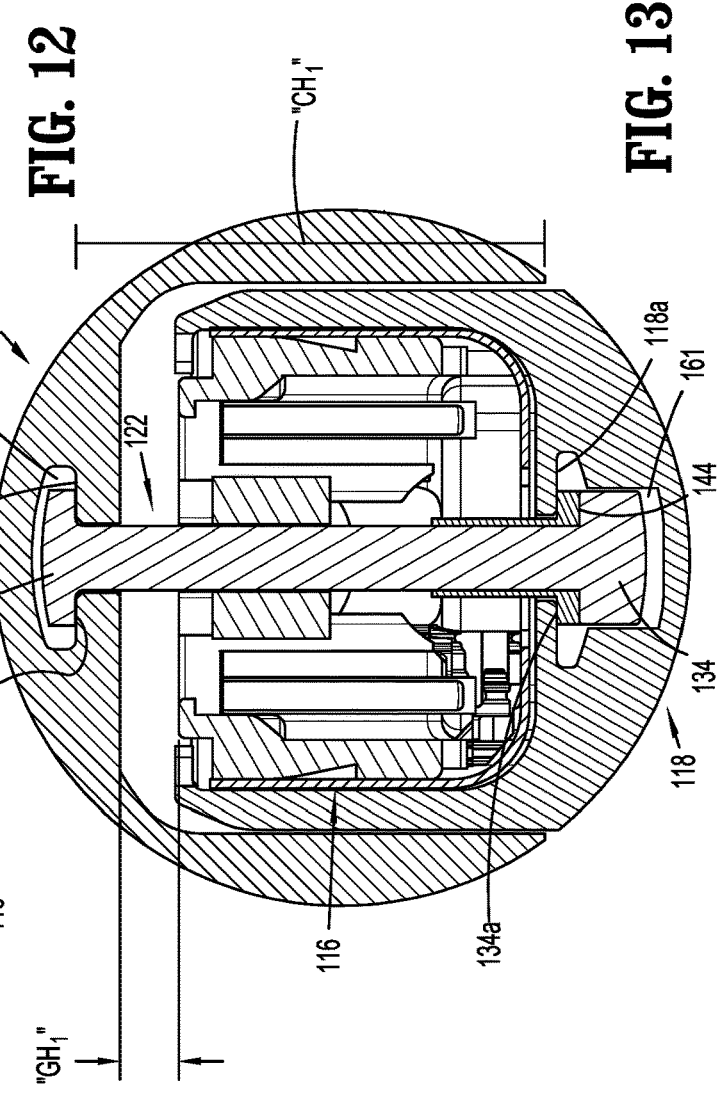
FIG. 13 is a cross-sectional view taken along section line 13-13 shown in FIG. 12.

FIGS. 12 and 13 illustrate the jaw assembly 106 of the tool assembly 104 of the stapling device 10 with the drive assembly 120 in the first configuration and in a partially advanced position, i.e., a pre-fired position in which the jaw assembly 106 is in the clamped position. When the drive assembly 120 is moved to the partially advanced position, receipt of the upper flange portion 132 of the dynamic clamping member 122 of the drive assembly 120 in the channel 151 of the anvil assembly 114 and engagement of the clamping surface 132a of the upper flange portion 132 of the dynamic clamping member 122 with the inner clamping surface 114a of the anvil assembly 114 causes the anvil assembly 114 to pivot relative to the cartridge assembly 116 to the clamped position. When the drive assembly 120 is in the first configuration and in the partially advanced position, the tissue contacting surfaces 114b, 116b of the anvil assembly 114 and the cartridge assembly 116, respectively, are spaced to define a first gap height "GH1". Continued advancement of the drive assembly 120 through the jaw assembly 106 to an advanced position effects the stapling (and cutting) of tissue as is known in the art.

FIG. 14 illustrates the drive assembly 120 of the loading unit 100 in the second configuration. More particularly, the adjustment beam 126 of the drive assembly 120 is in its proximal-most position relative to the drive beam 124 of the drive assembly 120, with the opening 127 in the adjustment beam 126 in alignment with the third opening 131c in the drive member 122. When the drive assembly 120 is in the second configuration, the clamping surface 132a of the upper flange portion 132 of the dynamic clamping member 122 and the clamping surface 144a of the adjustment flanges 144 of the engagement portion 140 of the adjustment beam 126 are spaced to define a second clamp height "CH2" that is less than the first clamp height "CH1". When the drive assembly 120 is in the second configuration, the stapling device 10 is configured to accommodate thinner tissue than when the drive assembly 120 is in the first configuration.

Figure 16:
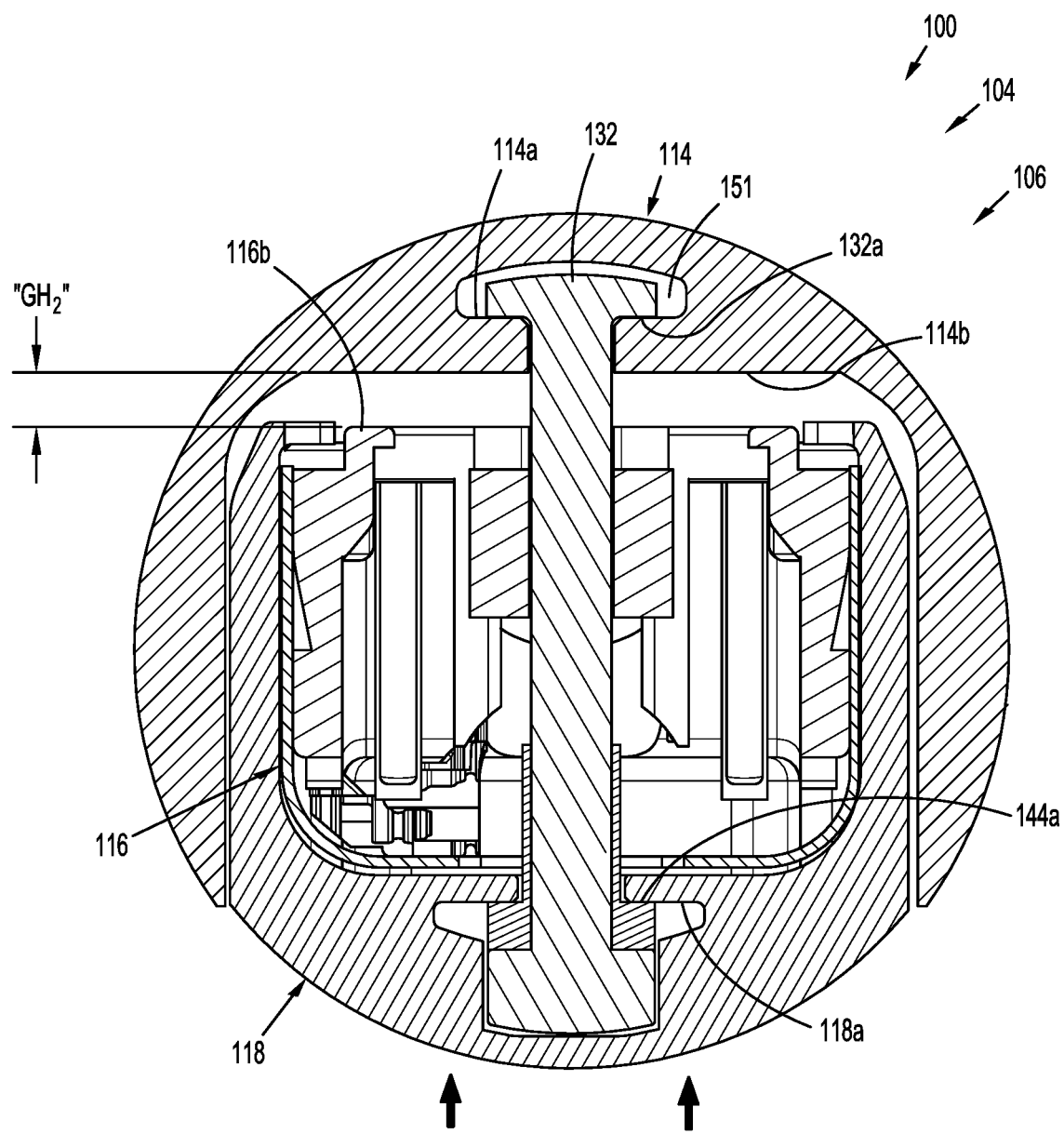
FIG. 16 is a cross-sectional view taken along section line 16-16 shown in FIG. 15.

FIGS. 15 and 16 illustrate the jaw assembly 106 of the tool assembly 104 of the stapling device 10 (FIG. 1) with the drive assembly 120 in the second configuration, and in the partially advanced position. In the partially advanced position, receipt of the upper flange portion 132 of the dynamic clamping member 122 in the channel 151 of the anvil assembly 114 and engagement of the clamping surfaces 132a of the upper flange portion 132 with the inner clamping surface 114a of the anvil assembly 114 causes the anvil assembly 114 to pivot relative to the cartridge assembly 116 to the clamped position. When the drive assembly 120 is in the second configuration and in the partially advanced position, the tissue contacting surfaces 114b, 116b of the anvil assembly 114 and the cartridge assembly 116, respectively, are spaced to define a second gap height "GH2". Continued advancement of the drive assembly 120 through the jaw assembly 106 effects the stapling of tissue as is known in the art.

Although the clamp height "CH" is shown and described as having a fixed distance once the adjustment beam 126 is secured relative to the drive beam 124, it is envisioned that the adjustment beam 126 may be moved relative to the drive beam 124 during the stapling procedure, i.e., as the drive assembly 120 is advanced through the jaw assembly 106, to adjusted the clamping height "CH" as the drive assembly 120 is advanced. The adjustment of the clamping height "CH" may be manual or automatic. For example, in smart staplers, i.e., staplers with sensors, the sensors will sense the tissue thickness and change the tissue gap as the stapler is fired, and in non-smart staplers, a biasing member maintains a specific pressure on the tissue independent of the tissue gap height.

Although the adjustment mechanism shown and described above relates to powered surgical staplers, the aspects of the disclosure may be modified for use on manually actuated stapling devices.

Figure 17:
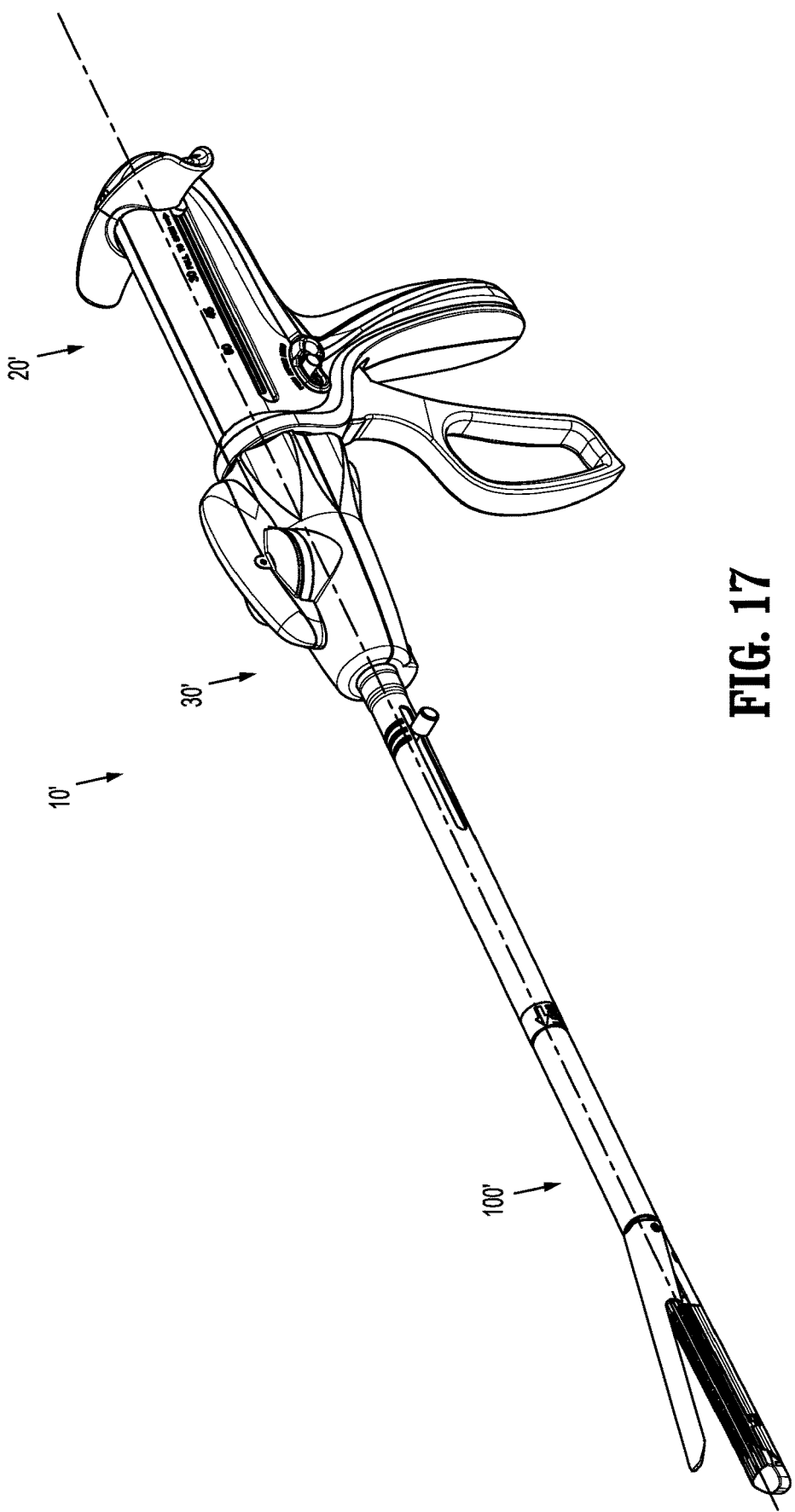
FIG. 17 is a side, perspective view of a manual surgical stapling device including a loading unit having a tool assembly in an open position according to other aspects of the disclosure.

FIG. 17 illustrates a manual surgical stapling device according to exemplary aspects of the disclosure, shown generally as stapling device 10'. The stapling device 10' includes a manual handle assembly 20' including an adapter assembly 30', and a loading unit 100' that is releasably secured to the adapter assembly 30'.

Although shown and described as used with hand-held actuation mechanisms, it is envisioned that the aspects of the disclosure may be modified for use remotely, i.e., with robotic systems (not shown).

Figure 18:
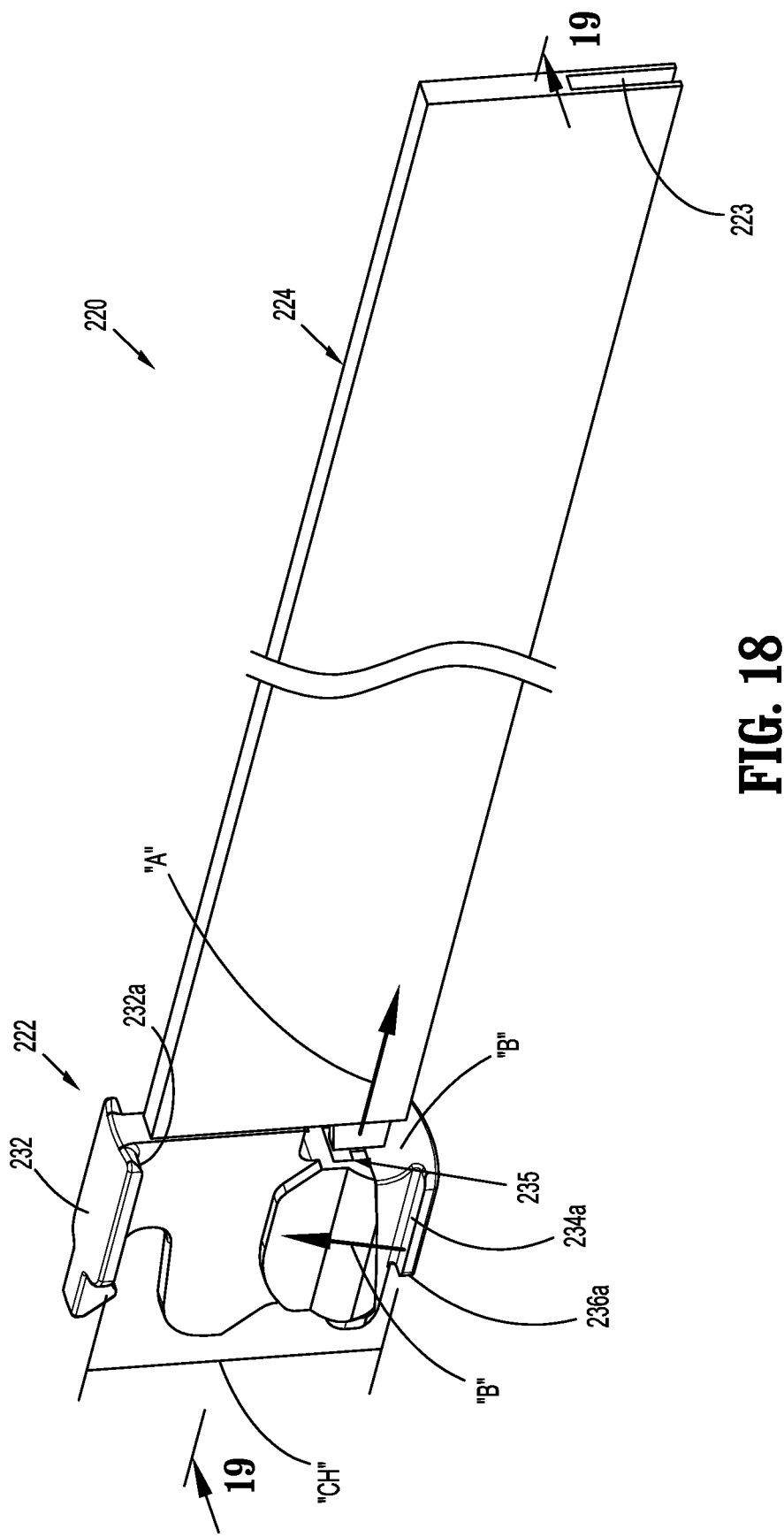
FIG. 18 is an enlarged, side perspective view of an alternate version of the drive assembly shown in FIG. 4.
Figure 19:
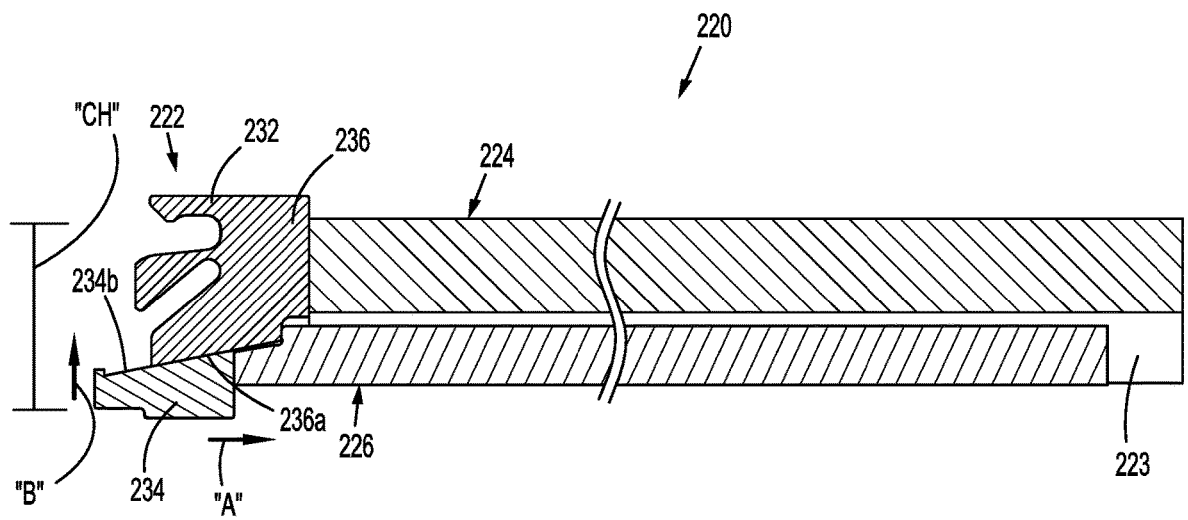
FIG. 19 is a side, cross-sectional view taken along section line 19-19 shown in FIG. 18.

FIGS. 18 and 19 illustrate a drive assembly according to other aspects of the disclosure shown generally as drive assembly 220. The drive assembly 220 is similar to the drive assembly 120 described hereinabove and will only be described in detail as relates to the differences therebetween.

The drive assembly 220 includes a dynamic clamping assembly 222, a drive beam 224, and an adjustment beam 226 (FIG. 19) slidably disposed relative to the drive beam 222 within a slot 223 formed in the drive beam 222. The dynamic clamping assembly 222 includes a clamping member 223, and a lower flange member 234. The clamping member 223 includes an upper flange member 232 and a vertical strut 236. The lower flange member 234 is secured to the vertical strut 236 of the clamping member 223 by a dovetail connection 235 (FIG. 18), or in any other suitable manner. The adjustment beam 226 is secured to the lower flange member 234 in any suitable manner and operates to move the lower flange member 234 along a longitudinal axis of the drive assembly 220 relative to the vertical strut 236. The lower flange member 234 and the vertical strut 236 include abutting inclined surfaces 234b, 236a. Longitudinal movement of the lower flange member 234 relative to the vertical strut 236 varies the distance between a clamping surface 232a (FIG. 18) of the upper flange portion 232 of the clamping member 223 and a clamping surface 234a (FIG. 18) of the lower flange member 234, e.g., a clamping height "CH".

Figure 20:
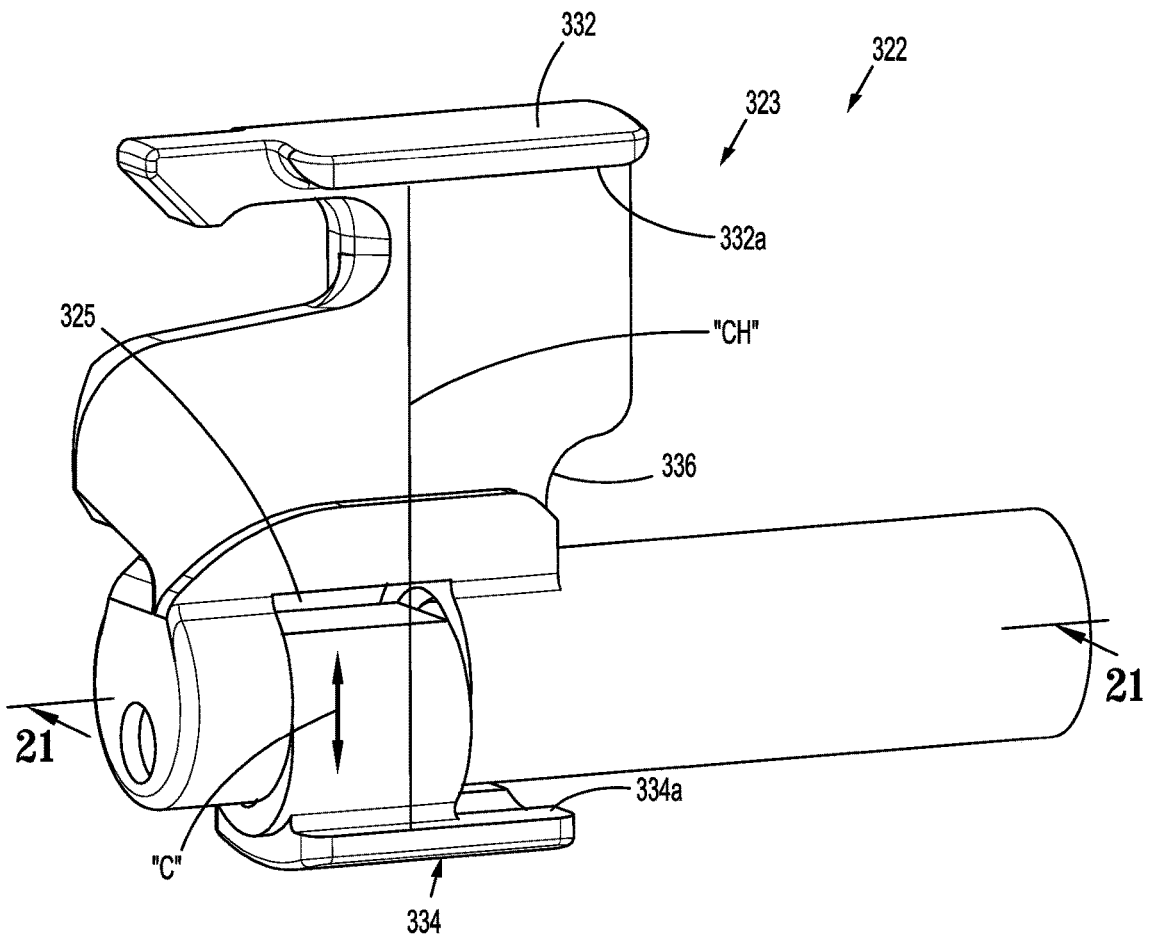
FIG. 20 is a side, perspective view of various aspects of another alternate version of the drive assembly shown in FIG. 4.
Figure 21:
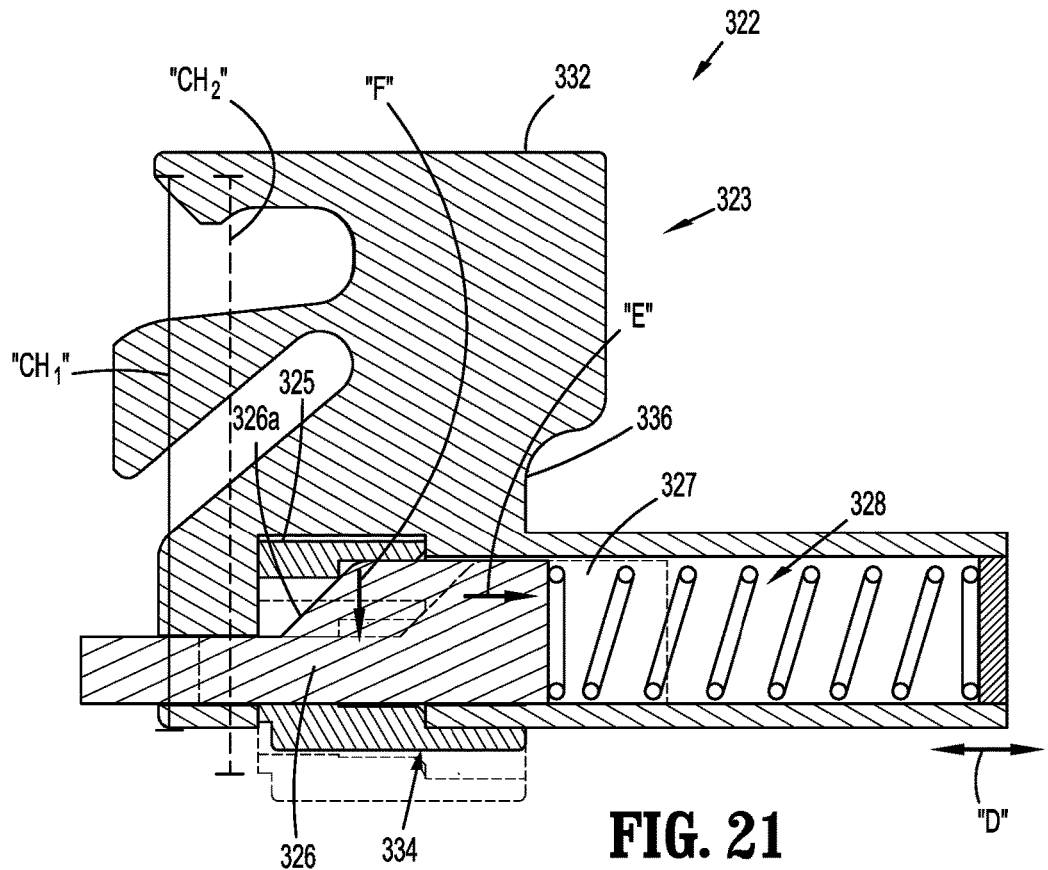
FIG. 21 is a cross-sectional view taken along section line 21-21 shown in FIG. 20.

As shown in FIGS. 18 and 19, the drive assembly 220 is in a first configuration, with the adjustment beam 226 in a distal-most position relative to the drive beam 224. When the drive assembly 220 is in the first configuration, the clamping height "C" is a first distance. As with drive assembly 120, described above, longitudinal movement of the adjustment beam 226 relative to the drive beam 224, as indicated by arrows "A", moves the inclined surface 234b of the lower flange member 234 relative the inclined surface 236a of the vertical strut such that the lower flange member 234 moves towards the upper flange portion 232, as indicated by arrow "B", to adjust the clamping height "CH" (FIG. 19) between minimum and maximum positions FIGS. 20 and 21 illustrate a dynamic clamping assembly according to another aspect of the disclosure shown generally as dynamic clamping assembly 320. The dynamic clamping assembly 320 is similar to the dynamic clamping assembly 222 described hereinabove and will only be described in detail as relates to the differences therebetween.

The dynamic clamping assembly 322 includes a clamping member 323 and a lower flange member 334. The clamping member 323 includes an upper flange portion 332 and a vertical strut 336. The lower flange member 334 is supported within a slot 325 of in the vertical strut 336. More particularly, the lower flange member 334 is movable vertically within the slot 325 perpendicular to a longitudinal axis of the dynamic clamping assembly 322, as indicated by arrow "C" in FIG. 21. In this manner, a distance between a clamping surface 332a of the upper flange portion 332 and a clamping surface 334a of the lower flange member 334, e.g., a clamping height "CH", may be adjusted by raising or lowering the lower flange member 334 relative to the vertical strut 336.

An adjustment member 326 (FIG. 21) extends through a cylindrical passage 327 in the vertical strut 336 and through the lower flange member 334. The adjustment member 326 is biased distally by a spring member 328 (FIG. 21). The adjustment member 326 includes an inclined surface 326a that is configured to engage the lower flange member 334 to change the relative position of the upper flange portion 332 and the lower flange member 334, respectively, in response to a change in the longitudinal position of the adjustment member 326 relative to the clamping member 323.

A plug member 324 secures the spring member 328 within the cylindrical passage 237. Longitudinal movement of the plug member 324 relative to the vertical strut 336 increase and decrease the compressive force on the spring member 328. By reducing the biasing force provided by the spring member 328 to the adjustment member 326, the adjustment member 326 is able to move relative to the lower flange member 334. For example, the bias on the spring member 328 may be effected by a threaded rod (not shown) extending through the loading unit, e.g., loading unit 100 (FIG. 1). Rotation of the threaded rod in a first direction would cause retraction of the plug 234 and thus, decompression of the spring member 328, thereby permitting proximal movement of the adjustment member 326. Conversely, rotation of the threaded rod in a second direction would cause advancement of the plug 328, and thus, compress the spring member 328 thereby causing distal movement of the adjustment member 326.

When the adjustment member 326 is in its distal-most position, as shown in FIG. 21, the dynamic clamping assembly 322 defines a first clamping height "CH1". Retraction of the adjustment member 326, as indicated by arrow "E" in FIG. 21, to its proximal-most position, causes the lower flange member 334 to move away from upper flange portion 332, as indicated by arrow "F" in FIG. 21". When the adjustment member 326 is in its proximal-most position (FIG. 21, shown in phantom), the dynamic clamping assembly 322 defines a second clamping height "CH2". The second clamping height "CH2" is greater than the first clamping height "CH1". By positioning the adjustment member 326 with the inclined surface 326a aligned with the lower flange member 334, i.e., between its proximal-most and distal-most positions, the adjustment member 326 may be positioned to create a clamping height "CH" between the first and second clamping heights "CH1" and "CH2".

Figure 22:
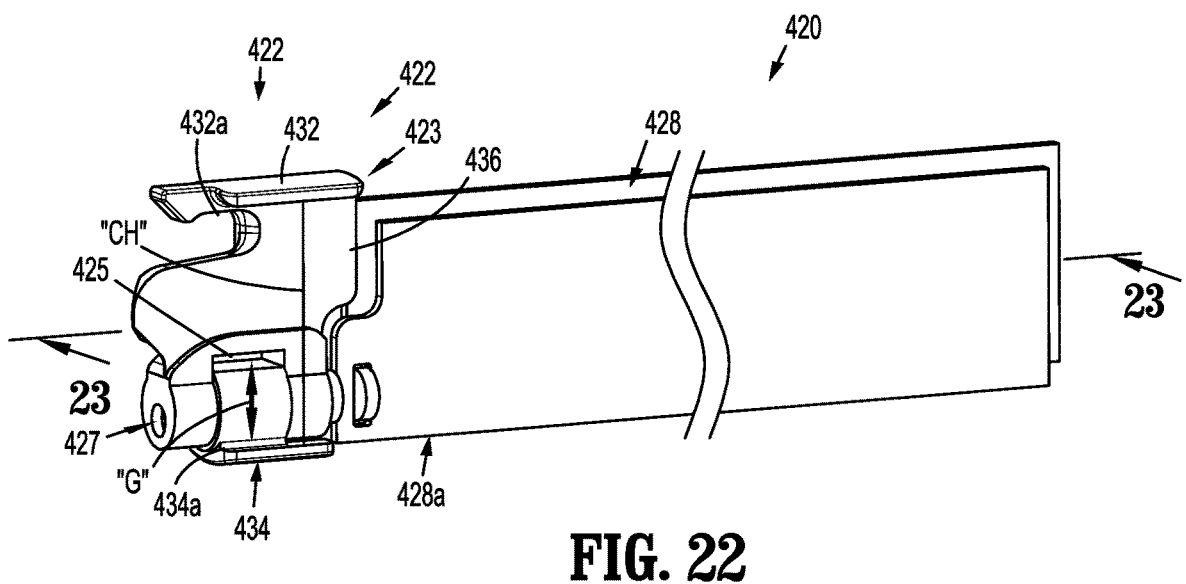
FIG. 22 is a side perspective view of yet another alternate version of the drive assembly.
Figure 23:
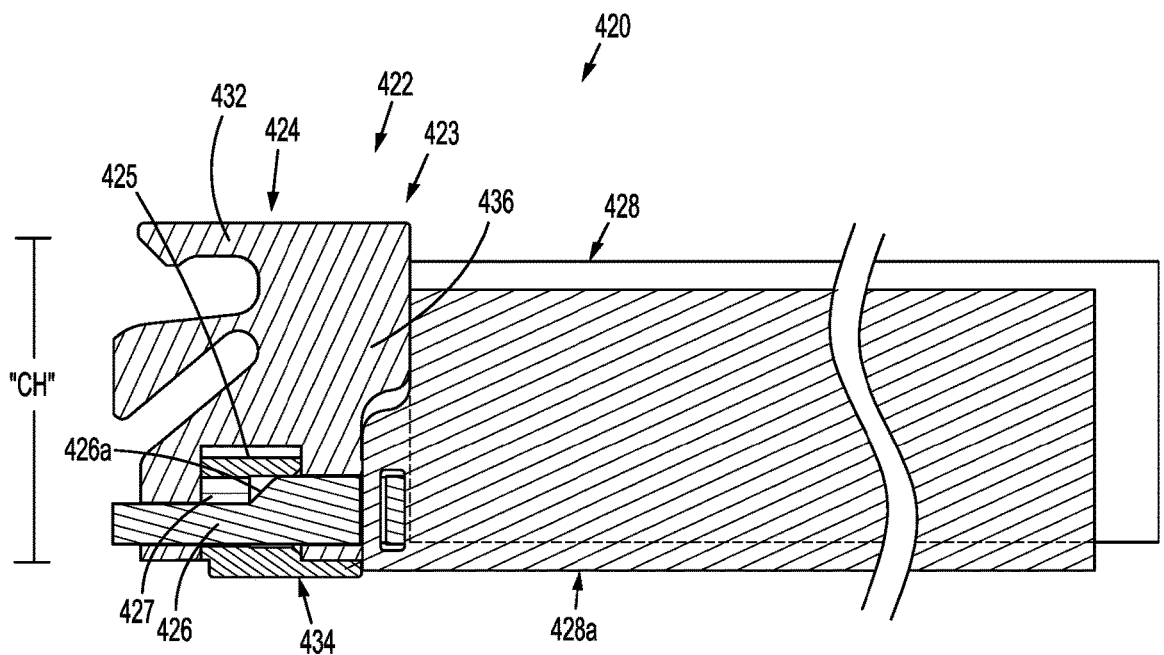
FIG. 23 is a side cross-sectional view taken along section line 23-23 shown in FIG. 22.

FIGS. 22 and 23 illustrate a drive assembly according to another aspect of the disclosure shown generally as drive assembly 420. The drive assembly 420 includes a dynamic clamping assembly 422 substantially similar to the dynamic clamping assembly 322 described hereinabove and will only be described in detail as relates to the differences therebetween.

The dynamic clamping assembly 422 includes a clamping member 423 and a lower flange member 434. The clamping member 423 includes an upper flange portion 432 and a vertical strut 436. The lower flange member 434 is supported within a slot 425 of the vertical strut 436 and is movable vertically within the slot 425 perpendicular to a longitudinal axis of the dynamic clamping assembly 422, as indicated by arrow "G" in FIG. 22. In this manner, a clamping height "CH" defined between a clamping surface 432a (FIG. 22) of the upper flange portion 432 and a clamping surface 434a of the lower flange member 434 may be adjusted by raising or lowering the lower flange member 434 relative to the vertical strut 436.

An adjustment member 426 extends through a cylindrical passage 427 (FIG. 22) in the vertical strut 436 and through the lower flange member 434. An adjustment beam 428a is secured to and extends from the adjustment member 426. The adjustment beam 428a extends along an axis that is parallel to a drive beam 428 that extends from the clamping member 423. The adjustment member 426 is movable between an advanced position (FIG. 22) and a retracted position by moving the adjustment beam 428a relative to the drive beam 428.

The adjustment member 426 includes an inclined surface 426a that is positioned to engage the lower flange member 434 depending on the longitudinal position of the adjustment member 426 relative to the clamping member 423. When the adjustment member 426 is in its distal-most position, as shown in FIG. 23, the clamping height "CH" is a first distance, and when the adjustment member 426 is in its proximal-most position (not shown), the clamping height "CH" is a second distance. The second distance is greater than the first distance. By positioning the adjustment member 426 with the inclined surface 426a aligned with the lower flange member 434, i.e., between its proximal-most and distal-most positions, the clamping height "CH" may be adjusted between the first and second distances.

Figure 24:
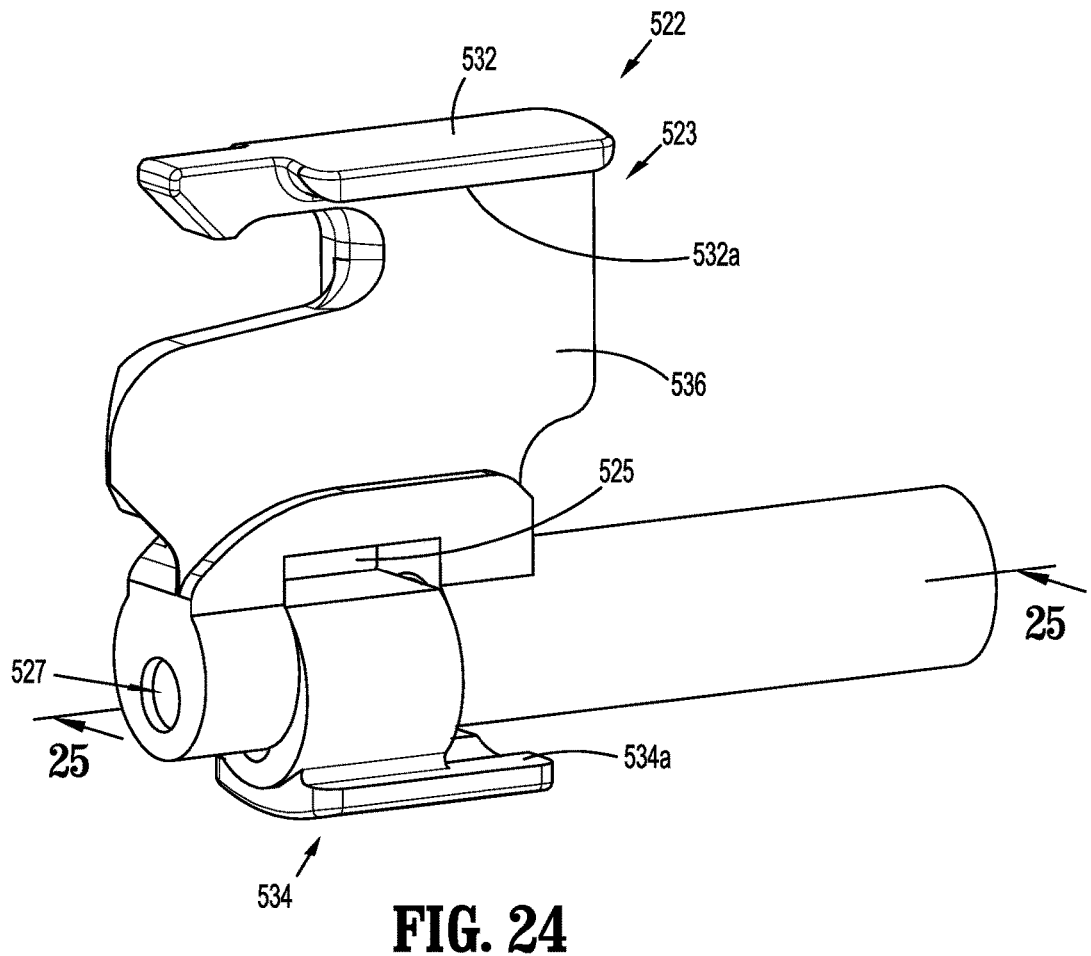
FIG. 24 is a side, perspective view of a dynamic clamping member of still another alternative version of the drive assembly.
Figure 25:
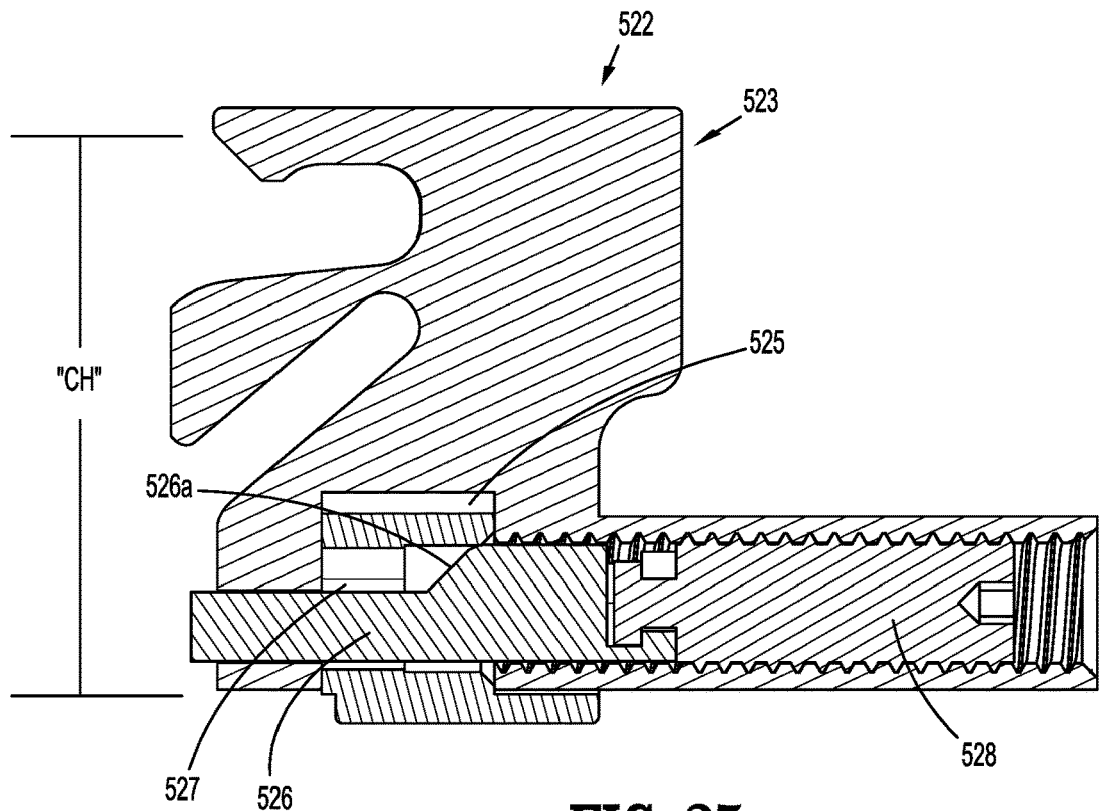
FIG. 25 is a side, cross-sectional view taken along section line 25-25 shown in FIG. 24.

FIGS. 24 and 25 illustrate a dynamic clamping assembly according to another aspect of the disclosure shown generally as dynamic clamping assembly 522. The dynamic clamping assembly 522 is similar to the dynamic clamping assembly 322 described hereinabove and will only be described in detail as relates to the differences therebetween.

The dynamic clamping assembly 522 includes a clamping member 523 and a lower flange member 534. The clamping member 523 includes an upper flange portion 532 and a vertical strut 536. The lower flange member 534 is supported within a slot 525 of the vertical strut 536 and is movable vertically within the slot 525 perpendicular to a longitudinal axis of the dynamic clamping assembly 522. In this manner, a clamping height "CH" defined between a clamping surface 532a (FIG. 24) of the upper flange portion 532 and a clamping surface 534a of the lower flange member 534 may be adjusted by raising or lowering the lower flange member 534 relative to the vertical strut 536.

An adjustment member 526 extends through a cylindrical passage 527 in the vertical strut 536 and through the lower flange member 534. The adjustment member 526 includes an inclined surface 526a configured to engage the lower flange member 534 depending on the longitudinal position of the adjustment member 526 relative to the clamping member 523. The adjustment member 526 is moveable along a longitudinal axis of the dynamic clamping assembly 522 by a threaded adjustment shaft 528. By rotating the adjustment shaft 528, the adjustment member 526 moves relative to the lower flange member 534.

When the adjustment member 526 of the dynamic clamping assembly 522 is in its distal-most position, as shown in FIG. 25, a clamping height "CH" is a first distance, and when the adjustment member 526 is in its proximal-most position (not shown), the clamping height "CH" is a second distance. The second distance is greater than the first distance. By positioning the adjustment member 526 with the inclined surface 526a aligned with the lower flange member 534, i.e., between its proximal-most and distal-most positions, the clamping height "CH" may be adjusted between the first and second distances.

Figure 26:
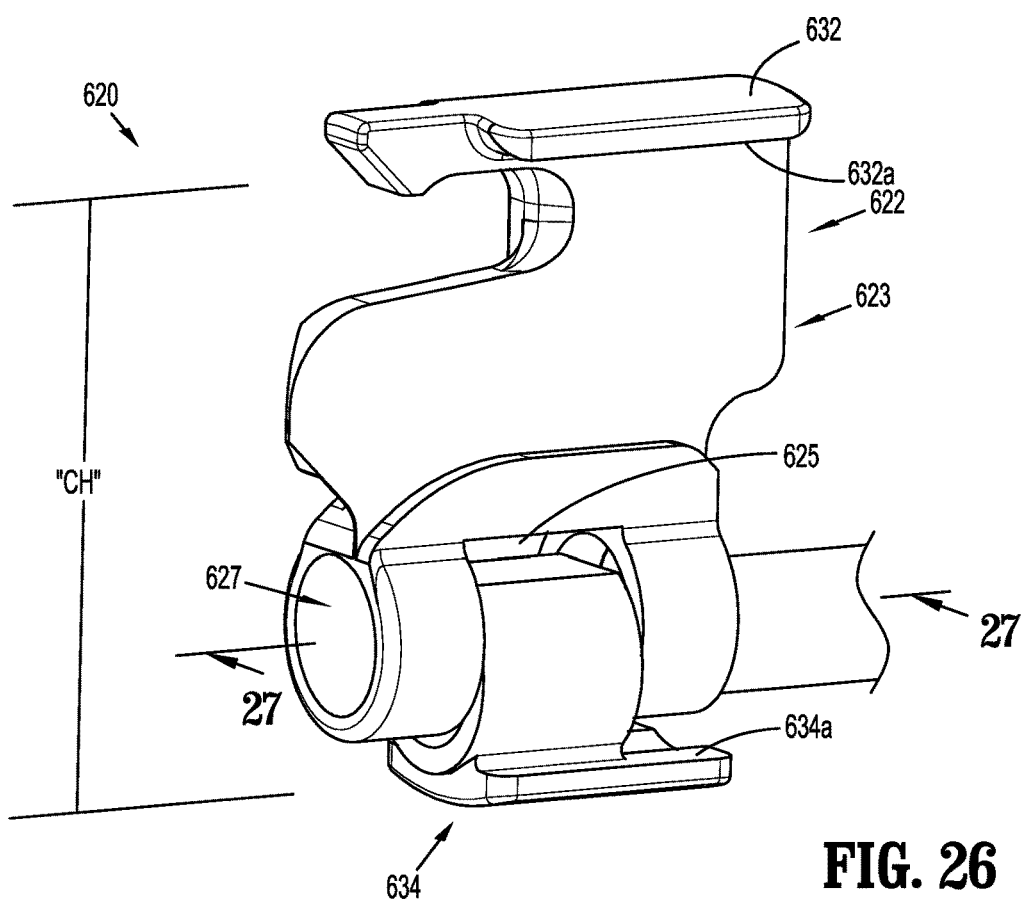
FIG. 26 is a side, perspective view of a dynamic clamping member of still yet another alternative version of the drive assembly.
Figure 27:
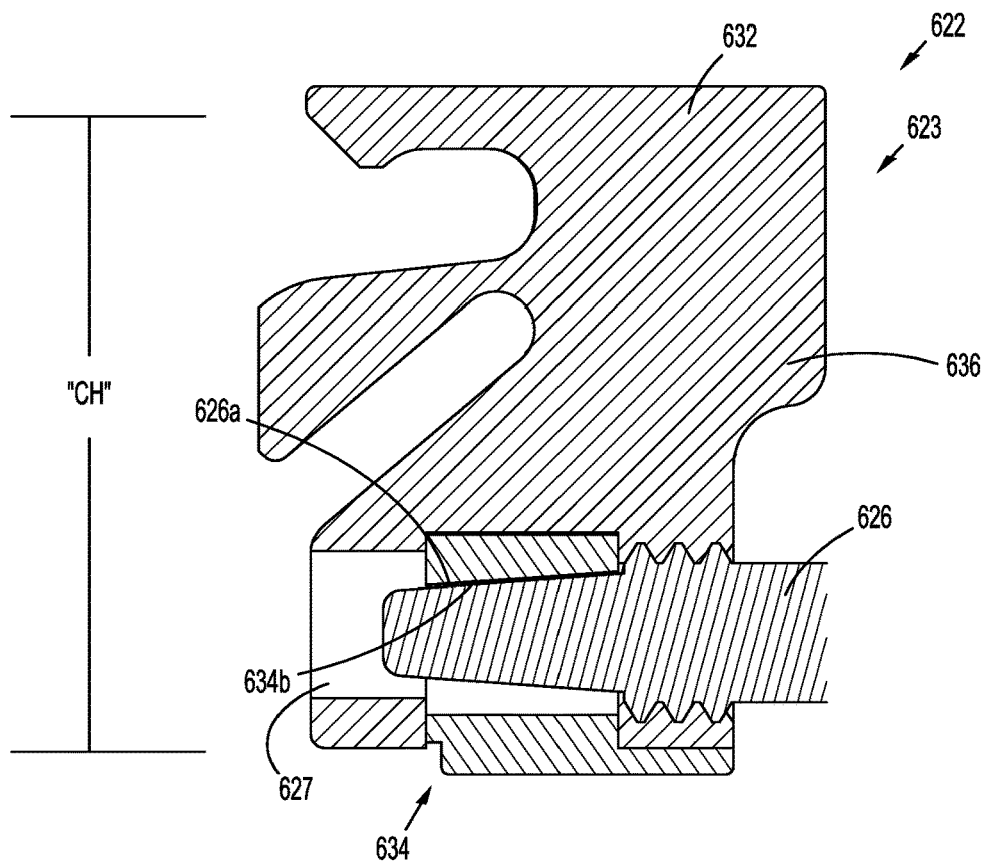
FIG. 27 is a side, cross-sectional view taken along section line 27-27 shown in FIG. 26.

FIGS. 26 and 27 illustrate a dynamic clamping assembly according to another aspect of the disclosure shown generally as dynamic clamping assembly 622. The dynamic clamping assembly 622 is similar to the dynamic clamping assemblies 322, 522 described hereinabove and will only be described in detail as relates to the differences therebetween.

The dynamic clamping assembly 622 includes a clamping member 623 and a lower flange member 634. The clamping member 623 includes an upper flange portion 632 and a vertical strut 636. The lower flange member 634 is supported within a slot 625 of the vertical strut 636 and is movable vertically within the slot 625 perpendicular to a longitudinal axis of the dynamic clamping assembly 622. In this manner, a clamping height "CH" defined between a clamping surface 632a (FIG. 26) of the upper flange portion 632 and a clamping surface 634a (FIG. 26) of the lower flange member 634 may be adjusted by raising or lowering the lower flange member 634 relative to the vertical strut 636.

An adjustment member 626 (FIG. 27) extends through a cylindrical passage 627 in the vertical strut 636 and through the lower flange member 634. The adjustment member 626 includes a conical distal portion 626a that is configured to engage an inclined surface 634b of the lower flange member 634. Depending on the longitudinal position of the adjustment member 626 relative to the clamping member 623 the clamping height "CH" may be adjusted. The adjustment member 626 is moveable along a longitudinal axis of the dynamic clamping assembly 622 by a threaded engagement with the vertical strut 636 of the clamping member 623. By rotating the adjustment member 626, the adjustment member 626 move relatives to the lower flange member 634.

When the adjustment member 626 of the drive is in its distal-most position, as shown in FIG. 27, the clamping height "CH" is a first distance, and when the adjustment member 626 is in its proximal-most position (not shown), the clamping height "CH" is a second distance. The second distance is greater than the first distance. By positioning the adjustment member 626 anywhere between its proximal-most and distal-most positions, the clamping height "CH" may be adjusted between the first and second distances. It is envisioned that the adjustment member 626 may operate as a drive member for advancing the dynamic clamping assembly 622 through a jaw assembly, for example, jaw assembly 106 (FIG. 1). Alternatively, the dynamic clamping assembly 622 may be advanced by a drive member (not shown).

Figure 28:
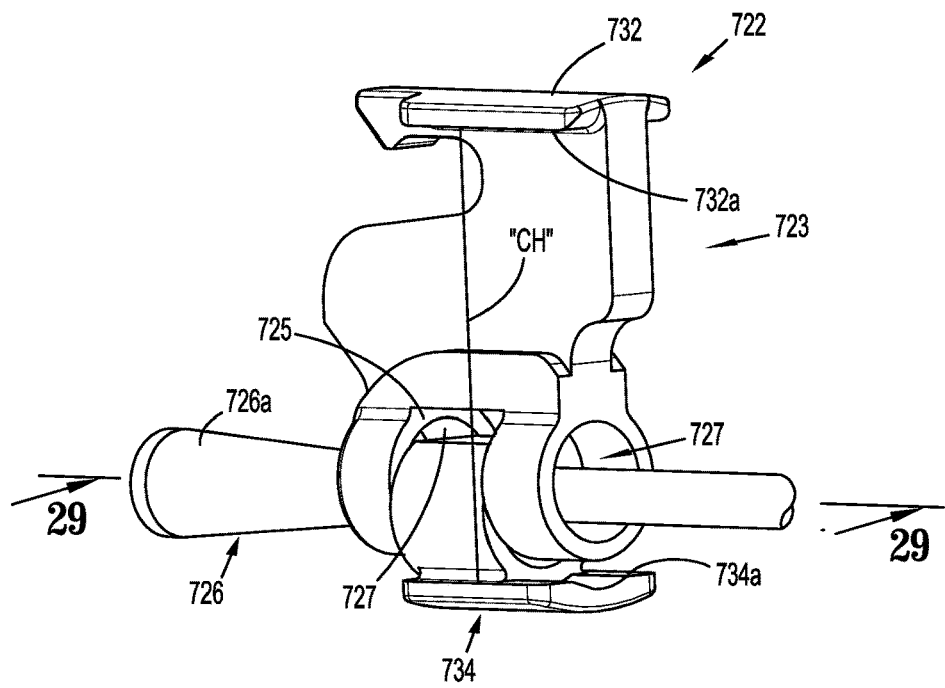
FIG. 28 is a side, perspective view of a dynamic clamping member of another alternate version of the drive assembly.
Figure 29:
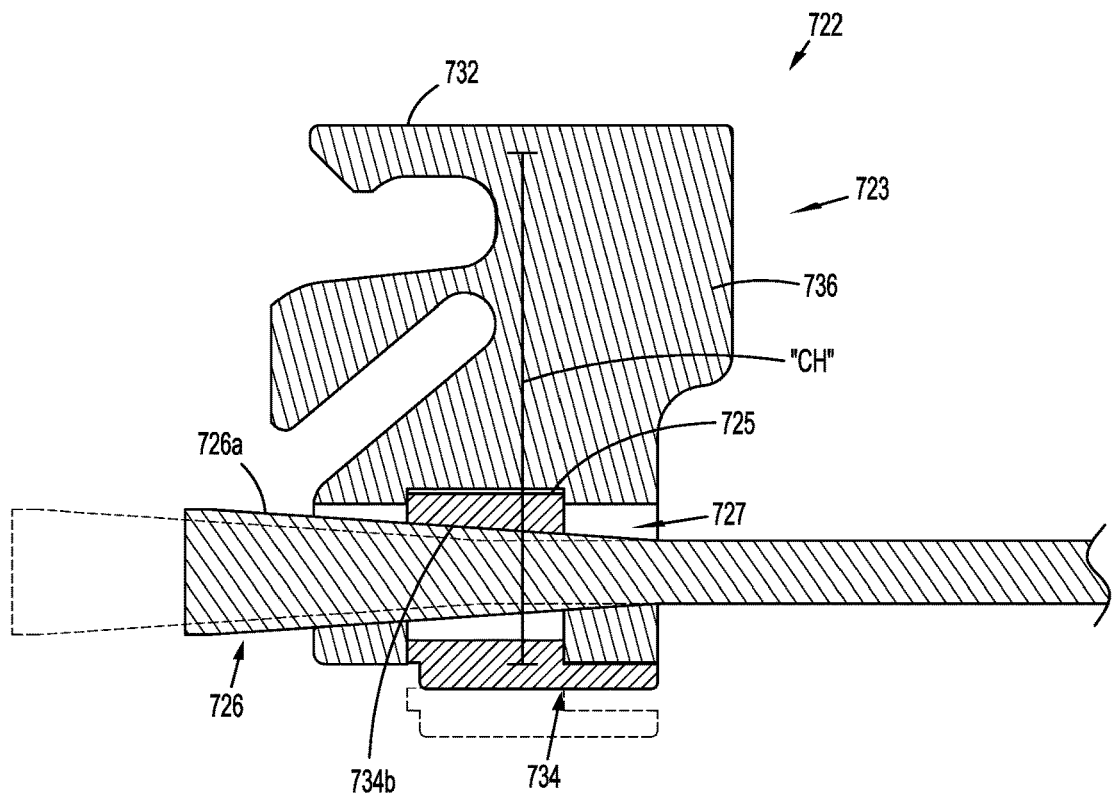
FIG. 29 is a side, cross-sectional view taken along section line 29-29 shown in FIG. 28.

FIGS. 28 and 29 illustrate a dynamic clamping assembly according to another aspect of the disclosure shown generally as dynamic clamping assembly 722. The dynamic clamping assembly 722 is similar to the dynamic clamping assemblies 322, 522, 622 described hereinabove and will only be described in detail as relates to the differences therebetween.

The dynamic clamping assembly 722 includes a clamping member 723 and a lower flange member 734. The clamping member 723 includes an upper flange portion 732 and a vertical strut 736. The lower flange member 734 is supported within a slot 725 of the vertical strut 736 and is movable vertically within the slot 725, i.e., perpendicular to a longitudinal axis of the dynamic clamping assembly 722. In this manner, a clamping height "CH" defined between a clamping surface 732a (FIG. 28) of the upper flange portion 732 and a clamping surface 734a (FIG. 28) of the lower flange member 734 may be adjusted by raising or lowering the lower flange member 734 relative to the vertical strut 736.

An adjustment member 726 extends through and from a cylindrical passage 727 in the vertical strut 736 and through the lower flange member 734. The adjustment member 726 includes a conical portion 726a that is configured to engage an inclined surface 734b of the lower flange member 734. Depending on the longitudinal position of the adjustment member 726 relative to the clamping member 723, the clamping height "CH" may be adjusted. The adjustment member 726 may be moveable along a longitudinal axis of the dynamic clamping assembly 722 by a threaded engagement (not shown) with the vertical strut 736 of the clamping member 723. When the adjustment member 726 is in its proximal-most position relative to the clamping member 723, as shown in FIG. 29, a clamping height "CH" is a first distance, and when the adjustment member 726 is in its distal-most position (FIG. 29, shown in phantom) relative to the clamping member 723, the clamping height "CH" is a second distance. The second distance is greater than the first distance. By positioning the adjustment member 726 anywhere between its proximal-most and distal-most positions, the clamping height "CH" may be adjusted between the first and second distances.

Figure 30:
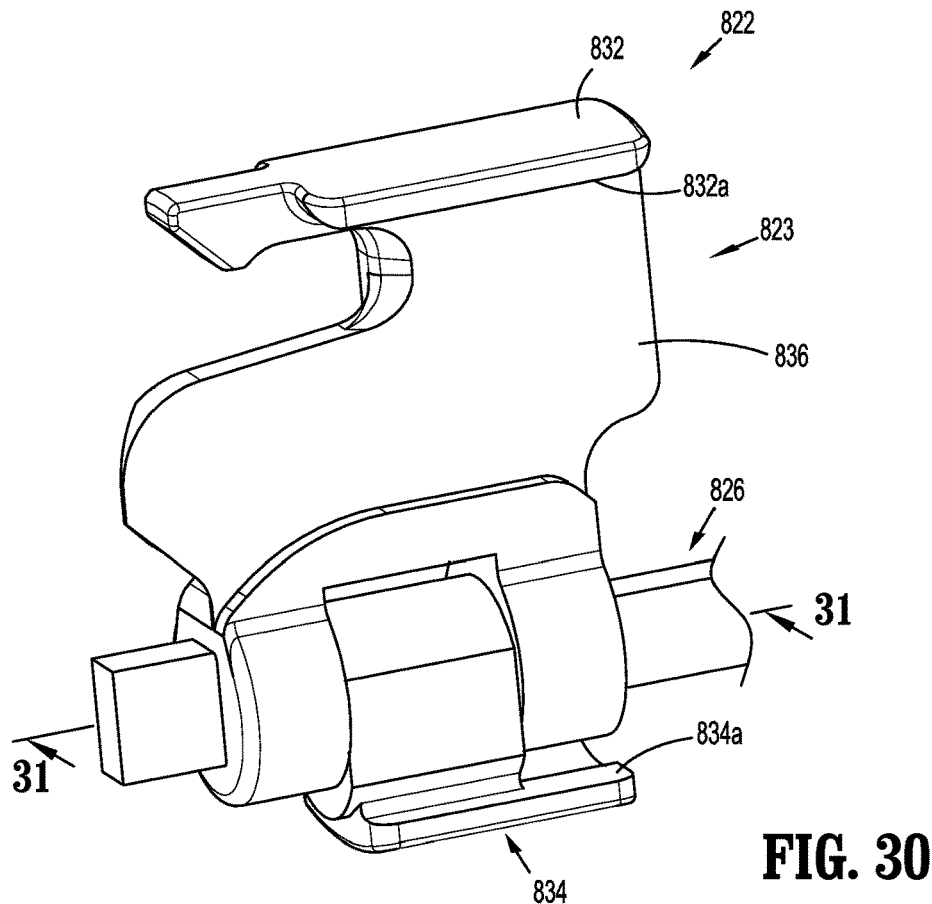
FIG. 30 is a side, perspective view of a dynamic clamping member and an adjustment beam of still another alternative version of the drive assembly.
Figure 31:
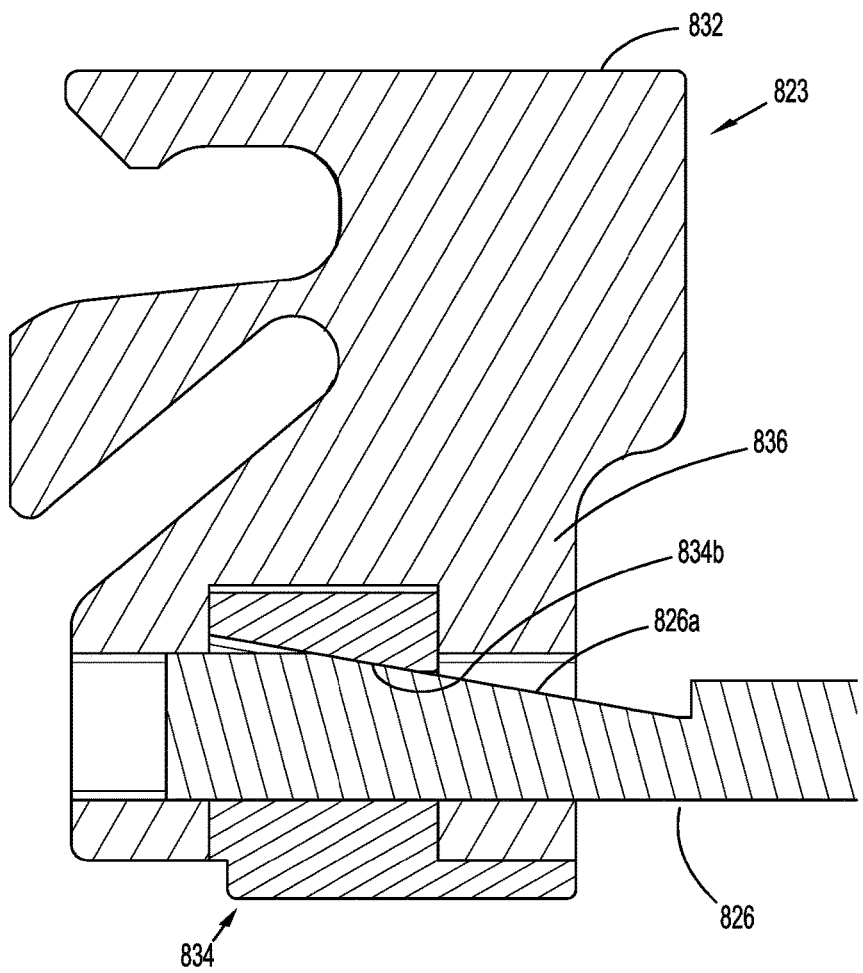
FIG. 31 is a side, cross-sectional view of the dynamic clamping member and the adjustment beam shown in FIG. 30.
Figure 32:
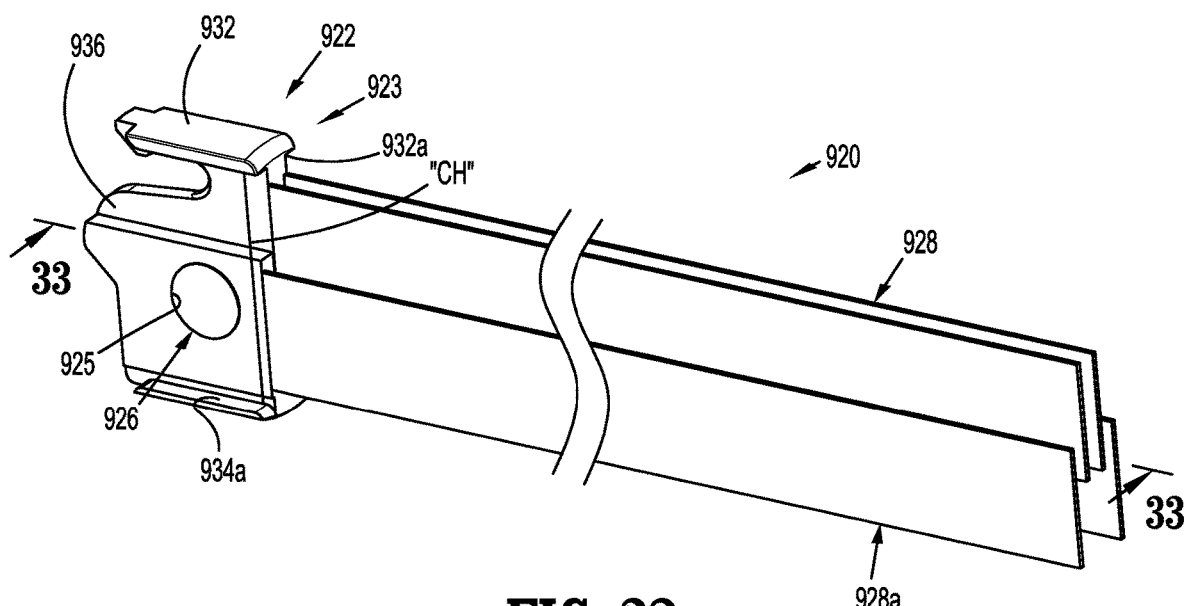
FIG. 32 is a side perspective view of still yet another alternate version of the drive assembly.

FIGS. 30 and 31 illustrate a dynamic clamping assembly according to another aspect of the disclosure shown generally as dynamic clamping assembly 822. The dynamic clamping assembly 822 is similar to the dynamic clamping assemblies described hereinabove and will only be described in detail as relates to the differences therebetween.

The dynamic clamping assembly 822 includes a clamping member 823 and a lower flange member 834. The clamping member 823 includes an upper flange portion 832 and a vertical strut 836. The lower flange member 834 is supported within a slot 825 of the vertical strut 836. More particularly, the lower flange member 834 is movable vertically within the slot 825, i.e., perpendicular to a longitudinal axis of the dynamic clamping assembly 822. In this manner, a clamping height "CH" defined between a clamping surface 832a (FIG. 30) of the upper flange portion 832 and a clamping surface 834a (FIG. 30) of the lower flange member 834 may be adjusted by raising or lowering the lower flange member 834 relative to the vertical strut 836.

An adjustment member 826 extends through and from a cylindrical passage 827 in the vertical strut 836 and through the lower flange member 834. The adjustment member 826 includes an inclined surface 826a that is configured to engage an inclined surface 834b of the lower flange member 834. Depending on the longitudinal position of the adjustment member 826 relative to the clamping member 823 the clamping height "CH" may be adjusted. The adjustment member 826 is moveable along a longitudinal axis of the dynamic clamping assembly 822 to adjust a clamping height "CH" of the dynamic clamping assembly 822.

When the adjustment member 826 is in its distal-most position, as shown in FIG. 31, the clamping height "CH" is a first distance, and when the adjustment member 826 is in its proximal-most position (not shown), the clamping height "CH" is a second distance. The second distance is greater than the first distance. By positioning the adjustment member 826 anywhere between its proximal-most and distal-most positions, the clamping height "CH" may be adjusted between the first and second distances.

FIGS. 32-35 illustrate a drive assembly according to another aspect of the disclosure shown generally as drive assembly 920. The drive assembly 920 is substantially similar to the drive assemblies described hereinabove and will only be described in detail as relates to the differences therebetween.

The drive assembly 920 includes a dynamic clamping assembly 922 having a clamping member 923 and a lower flange member 934. The clamping member 923 includes an upper flange portion 932 and a vertical strut 936. The lower flange member 934 is received about and supported by the vertical strut 936 and is movable vertically relative to the vertical strut 936, i.e., perpendicular to a longitudinal axis of the clamping member 922. In this manner, a clamping height "CH" defined between a clamping surface 932a (FIG. 30) of the upper flange portion 932 and a clamping surface 834a (FIG. 30) of the lower flange member 934 may be adjusted by raising or lowering the lower flange member 934 relative to the vertical strut 936.

An adjustment member 926 is supported within a cylindrical recess 925 defined by the vertical strut 936 and the lower flange member 934. The adjustment member 926 includes a cam member 926a. Depending on the rotational orientation of the adjustment member 926 relative to the clamping member 923, i.e., the position of the cam member 926a relative to the clamping member 923, the clamping height "CH" may be adjusted. The adjustment member 926 is rotatable about its central axis to adjust a clamping height "CH" of the dynamic clamping assembly 922.

When the adjustment member 926 is oriented with the cam member 926a in a six o'clock position, as shown in FIG. 34, the clamping height "CH" is a first distance, and when the adjustment member 926 is oriented in a twelve o'clock position (not shown), the clamping height "CH" is a second distance. The second distance is greater than the first distance. By positioning the adjustment member 926 anywhere between the six o'clock and twelve o'clock positions, the clamping height "CH" may be adjusted between the first and second distances.

It is envisioned that the orientation of the cam member 926a may be adjusted by moving an adjustment beam 928a of the drive assembly 920 relative to a drive beam 928 of the drive assembly 920. This may include a slotted, geared, or ratcheted arrangement, or other suitable configuration.

Persons skilled in the art will understand that the devices and methods specifically described herein and illustrated in the accompanying drawings are non-limiting exemplary aspects. It is envisioned that the elements and features illustrated or described in connection with the exemplary aspects may be combined with the elements and features of another without departing from the scope of the disclosure. As well, one skilled in the art will appreciate further features and advantages of the disclosure based on the above-described aspects. Accordingly, the disclosure is not to be limited by what has been particularly shown and described, except as indicated by the appended claims.

What is claimed is:

1. A surgical stapling device comprising:
a body portion defining a longitudinal axis having a proximal portion and a distal portion;
a tool assembly supported on the distal portion of the body portion, the tool assembly including an anvil assembly, a channel member pivotally supported relative to the anvil assembly, and a staple cartridge releasably disposed within the channel member, the tool assembly being movable from an open position to an approximated position, the staple cartridge supporting a plurality of staples and including an actuation sled movable between a sled retracted position and a sled advanced position to eject the plurality of staples from the staple cartridge; and a drive assembly movably supported within the tool assembly from a drive retracted position to a drive advanced position to move the tool assembly from the open position to the approximated position and to maintain the tool assembly in the approximated position, the drive assembly including a clamping member, an adjustment member, and an adjustment beam, the clamping member including a first clamping surface configured to engage the anvil assembly and the adjustment member including a second clamping surface configured to engage the staple cartridge, the first clamping surface spaced from the second clamping surface to define a clamping height, wherein the adjustment member is moveable relative to the clamping member between a first position and a second position to change the clamping height, the adjustment beam extending proximally from the adjustment member into the body portion and moveable to move the adjustment member between the first position and the second position.

2. The surgical stapling device of claim 1, wherein the first position of the adjustment member is longitudinally spaced from the second position of the adjustment member.

3. The surgical stapling device of claim 1, wherein the first position of the adjustment member is vertically spaced from the second position of the adjustment member.

4. The surgical stapling device of claim 1, wherein the channel member defines a slot and the adjustment member includes a flange, the flange being receivable within the slot of the channel member.

5. The surgical stapling device of claim 4, wherein the anvil assembly defines a slot and the clamping member includes a pair of flanges, the pair of flanges of the clamping member being receivable within the slot of the anvil assembly.

6. The surgical stapling device of claim 2, wherein the drive assembly further includes a drive beam and a securement mechanism for securing the adjustment beam to the drive beam.

7. The surgical stapling device of claim 6, wherein the securement member includes an adjustment knob and a threaded screw extending from the adjustment knob.

8. The surgical stapling device of claim 1, wherein movement of the drive assembly beyond a partially advanced position moves the actuation sled from the sled retracted position to the sled advanced position to eject the plurality of staples from the staple cartridge.

9. The surgical stapling device of claim 1, wherein the clamping member including an upper flange and a lower flange interconnected by a vertical strut, the clamping member being positioned to engage the actuation sled to move the actuation sled distally within the staple cartridge as the drive assembly moves from the drive retracted position towards the drive advanced position.

10. The surgical stapling device of claim 9, wherein the adjustment member includes an inclined surface, the clamping member includes an inclined surface, and movement of the adjustment member relative to the clamping member slides the inclined surfaces relative to each other.

11. A drive assembly for a surgical stapling assembly, the drive assembly comprising:

a clamping member having an upper flange portion and a vertical strut, the upper flange portion including a first clamping surface configured to engage an anvil assembly of the surgical stapling assembly;

a drive beam extending from the clamping member and configured for operable engagement with an actuation mechanism of the surgical stapling assembly;

an adjustment member spaced from the first clamping surface of the clamping member and including a second clamping surface configured to engage a cartridge assembly of the surgical stapling assembly, the first clamping surface spaced from the second clamping surface to define a clamping height, wherein the adjustment member is moveable relative to the clamping member between a first position and a second position to change the clamping height; and an adjustment beam extending proximally from the adjustment member along the drive beam and moveable to move the adjustment member between the first position and the second position.

12. The drive assembly according to claim 11, wherein the upper flange portion is configured to be received within a slot of the anvil assembly.

13. The drive assembly according to claim 12, wherein the adjustment member includes a flange portion configured to be received within a slot of a staple cartridge.

14. The drive assembly according to claim 11, further including a securement mechanism for securing the drive beam relative to the adjustment mechanism.

15. The drive assembly according to claim 14, wherein the securement mechanism is a threaded screw.

16. The drive assembly according to claim 11, wherein the first position of the adjustment member is longitudinally spaced from the second position of the adjustment member.

17. The surgical stapling device of claim 11, wherein the first position of the adjustment member is vertically spaced from the second position of the adjustment member.

* * * * *